(12) United States Patent
Rickles

(10) Patent No.: US 6,303,319 B1
(45) Date of Patent: Oct. 16, 2001

(54) CELL BASED ASSAY FOR IDENTIFYING SH2-DOMAIN-SPECIFIC SIGNAL TRANSDUCER ANTAGONIST

(75) Inventor: Richard J. Rickles, Somerville, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/101,927

(22) PCT Filed: Feb. 21, 1997

(86) PCT No.: PCT/US97/02635

§ 371 Date: Jul. 15, 1998

§ 102(e) Date: Jul. 15, 1998

(87) PCT Pub. No.: WO97/31113

PCT Pub. Date: Aug. 28, 1997

Related U.S. Application Data
(60) Provisional application No. 60/012,218, filed on Feb. 23, 1996.

(51) Int. Cl.[7] .................... G01N 33/53; G01N 33/567; C12Q 1/68; C12Q 3/00; C12Q 1/54
(52) U.S. Cl. .................... 435/7.1; 435/6; 435/4; 435/3; 435/14; 435/7.21; 435/7.95; 435/7.8; 435/69.2; 435/69.8; 435/69.9
(58) Field of Search .................... 435/6, 4, 3, 14, 435/7.1, 7.21, 7.95, 7.8, 69.2, 69.8, 69.9

(56) References Cited

U.S. PATENT DOCUMENTS

| | | | |
|---|---|---|---|
| 5,283,173 | 2/1994 | Fields | 435/6 |
| 5,352,660 | 10/1994 | Pawson | 514/12 |

FOREIGN PATENT DOCUMENTS

| | | |
|---|---|---|
| WO 94/07913 | 4/1994 | (WO) . |
| 95/24419 * | 9/1995 | (WO) . |

OTHER PUBLICATIONS

Xing et al.; Direct interaction of v–Src with the Focal. . . ; Molecular Biology of the Cell; vol. 5; pp. 413–421, Apr. 1994.*
Bu et al.; Analysis of the interaction of the zap–70 and syk protein–tyrosine kinases . . . ; Proc. Natl. Acad. Sci.; vol. 92; pp., 5106–5110, Apr. 1994.*
Xing et al.; "Direct interaction of v–SRC with the focal adhesion kinase mediated by the Src SH2 domain"; Molecular Biology of the Cell; vol. 5; pp. 413–421, Apr. 1994.*
Fields and Song, (1989) Nature 340:245–247.
Scherrer et al., (1993) Biochemistry 32:5381–5386.
Xing et al., (1994) Mol. Biol. Cell 5:413–421.
Osborne et al., (1995) Nature Biotechnology 13:1474–1478.
Chaudhuri et al., (1995) FEBS Lett. 357:221–226.
O'Neill et al., (1994) Mol. Cell. Biol 14:6433–6442.

* cited by examiner

Primary Examiner—Ali R. Salimi
Assistant Examiner—Bao Qun Li
(74) Attorney, Agent, or Firm—David L. Berstein

(57) ABSTRACT

The present invention provides methods and compositions for identifying inhibitors of the interaction between phosphopeptide binding pairs, i.e., a protein domain having at least one phosphopeptide binding domain and the phosphorylated ligands that bind these domains. These inhibitors may be used for pharmaceutical compositions and in therapeutic treatments for diseases in which a phosphopeptide domain binding is implicated.

11 Claims, 9 Drawing Sheets

US 6,303,319 B1

CELL BASED ASSAY FOR IDENTIFYING SH2-DOMAIN-SPECIFIC SIGNAL TRANSDUCER ANTAGONIST

This appln is a 371 of PCT/US97/02635 filed Feb. 21, 1997 and also claims benefit of provisional No. 60/012,218 filed Feb. 23, 1996.

TECHNICAL FIELD OF THE INVENTION

This invention relates to materials and methods for the identification of inhibitors of certain molecular interactions.

BACKGROUND OF THE INVENTION

Cellular signal transduction, i.e., the series of events leading from extracellular events to intracellular sequelae, is an aspect of cellular function in both normal and disease states. Numerous proteins that function as signal transducing molecules have been identified, including receptor and non-receptor tyrosine kinases, phosphatases and other molecules with enzymatic or regulatory activities. These molecules generally demonstrate the capacity to associate specifically with other proteins to form a signaling complex that can alter cell activity.

Signaling proteins often contain domains of conserved sequence which serve as non-catalytic modules that direct protein-protein interactions during signal transduction. One such domain is the Src homology domain 2 (SH2), which is found in various combinations and locations in different proteins. For example, some members of the Src-family of tyrosine kinases, e.g., Abl, GRB2 and P13K, each contain one SH2 domain. Other tyrosine kinases, such as ZAP and Syk, contain two SH2 domains. The presence of multiple SH2 domains within a protein increases the variety of potential protein-protein interactions.

SH2 domains direct the association of specific proteins or protein domains by binding selectively and with specificity to protein sequences or motifs containing phosphotyrosine. For example, upon ligand binding, the PDGF beta-receptor dimerizes and autophosphorylates multiple tyrosine residues. This phosphorylation of tyrosine-containing protein motifs within the receptor triggers its physical association with SH2-containing proteins such as c-src, PLC-gamma, P13K and ras-GAP, forming a signaling complex. Other examples include the binding of the tandem SH2-containing protein Syk to tyrosine-phosphorylated motifs on the beta or gamma subunits of the IgE receptor, and the binding of the tandem SH2-containing protein ZAP-70 with tyrosine-phosphorylated motifs on subunits of the T cell receptor. Other protein receptors for tyrosine-phosphorylated protein domains are known and include the so-called phosphotyrosine binding domains ("PTBs") or phosphotyrosine interaction domains ("PIDs"). Many signaling pathways which play critical roles in disease processes are mediated by the binding of a phosphotyrosine-containing protein or protein domain with an SH2 or other protein receptor for a tyrosine-phosphorylated domain.

Pharmaceutical agents which interfere with the formation or stability of such signaling complexes may be used for precise intervention in these complex biological processes in order to treat or prevent the diseases or pathological effects mediated by such signaling. However, one common but significant problem when screening for pharmaceutically useful compounds that disrupt specific cellular events is deciphering their mechanism and specificity of action. Typically one searches for inhibition of a signaling cascade by measuring the effect of test compounds on an event several, if not many, steps downstream of a protein-protein interaction of particular interest. To the extent that a compound may exert its effects on any number of intermediate steps, the results of such experiments can be difficult to interpret.

A so-called "two-hybrid" interaction assay described by Song and Fields, Nature, 340:245–247 (1989) has been used to detect the interactions of a variety of molecules. See also, Fields et al, U.S. Pat. No. 5,283,173 (Feb. 1, 1994). The two-hybrid assay is based on the observation that transcription factors contain separable functional modules that direct either DNA binding or transcription activation. A DNA binding domain expressed in cells will bind to DNA but not activate transcription as it lacks a transcription activation domain. Conversely, a transcription activation domain alone will not affect transcription in the absence of directed and/or intimate interaction with DNA such as would be provided by a DNA-binding domain. However, if the DNA binding domain and the transcription activation domains are each expressed as part of separate fusion proteins, and the fusion proteins are capable of associating, the "two-hybrid" complex so formed represents a reconstituted transcription factor (see FIG. 1). Such a reconstituted transcription factor is capable of initiating transcription of a reporter gene (e.g., a gene for a conveniently detectable marker such as beta-galactosidase or alkaline phosphatase (SEAP) or a protein important for cell viability) located downstream of DNA binding sites recognized by the DNA-binding domain. The amount of reporter gene expression, i.e., the amount of gene product produced, will reflect the extent to which the fusion proteins complex with one another. Compounds that block the association of the fusion proteins will reduce reporter gene expression.

The two-hybrid assay approach has been used to identify presumed SH2-dependent protein-protein interactions using yeast [Xing, Z. et al., Mol. Biol. Cell, 5:413–421 (1994) and Osborne, M. A. et al., Biotechnol., 13:1474–1478 (1995)]. In those experiments, protein binding pairs, rather than inhibitors of such binding, were identified. The two hybrid approach has also been used to detect the inhibition of certain protein-protein interactions in yeast, but not for inhibition of protein-protein interactions involving phosphorylated ligands and their receptors [Chaudhuri, B. et al., FEBS Lett., 357: 221–226 (1995)]. While a yeast-based two-hybrid approach may be useful for other purposes, it would not lend itself to screening for drugs to inhibit phosphopeptide-mediated interactions in mammalian cells since the use of yeast cells would limit the researcher, or at least the "hits", to the subset of compounds which are able to penetrate the yeast cell wall. This artificial limitation would incorporate into the experimental design the risk of missing important new compounds capable of blocking key signaling interactions in mammalian cells, but which are unable to penetrate yeast cells.

There thus remains a need in the art for improved methods and compositions for identifying inhibitors of phosphopeptide-mediated protein-protein binding in a wide variety of host cells.

SUMMARY OF THE INVENTION

The present invention addresses this need by providing a mechanism-based in vivo assay that allows the identification of inhibitory compounds that target key molecules involved in specific signal transduction pathways.

The invention provides a cell containing, and capable of expressing, recombinant DNA molecules encoding a pair of fusion proteins. One DNA molecule encodes a transcription activating fusion protein which comprises one or more transcription activation domains (TADs) and at least one member of a phosphopeptide binding pair, i.e., a phosphopeptide binding domain or peptide ligand therefor. Another DNA molecule encodes a DNA-binding fusion protein which comprises one or more DNA-binding domains (DBDs) and the other member of the phosphopeptide binding pair. The cell further contains a reporter gene which is linked to a DNA sequence to which the DNA-binding fusion protein is capable of binding. The reporter gene encodes a detectable gene product which is expressed when transcription of the reporter gene is activated, e.g. following association of the two fusion proteins to reconstitute an effective transcription factor. The engineered cell further contains a protein kinase capable of phosphorylating one or more of the tyrosine residues of the peptide ligand as is required for two-hybrid formation. The kinase may be endogenous to the cell or may be the gene product of an introduced, heterologous gene. In one embodiment one of the fusion proteins contains a kinase domain and thus provides its own kinase function. One or both of the fusion proteins may optionally contain a nuclear hormone-binding domain (HBD) permitting regulated sequestering or inactivation of the fusion protein. In such embodiments, addition of the hormone renders the HBD-bearing fusion protein available for two-hybrid formation. When the cell expresses the two fusion proteins, and the peptide ligand domain has become tyrosine phosphorylated, the two fusion proteins are capable of binding to each other via complexation of the phosphorylated peptide ligand of one fusion protein with the PBD of the other. So complexed, the fusion proteins are capable of detectably activating the transcription of the reporter gene linked to a DNA sequence recognized (i.e., bound) by the DNA-binding domain of one of the fusion proteins.

One object of the invention is to provide the above-described DNA molecules. Another is to introduce the DNA molecules into host cells to provide genetically engineered cells useful for conducting the assay methods described herein.

Another object of the invention is to provide a method for identifying the presence in a test composition of an inhibitor of the binding of a tyrosine-phosphorylated ligand with a phosphopeptide binding domain therefor or of a biological activity mediated by that phosphopeptide binding pair. This method involves culturing or maintaining the above-described genetically engineered cells in a medium suitable for cell growth, in the presence and absence of the test composition, and determining whether production of the detectable reporter gene product was diminished in the presence of the test composition. In practice, the test composition is added to the cells, e.g. to the medium in which the cells are cultured, and the culture is incubated under conditions permitting formation of a complex between the fusion proteins. In embodiments involving hormone regulation, the hormone may be added before, during or, as may often be preferable, after addition of the test composition. If binding of the DNA-binding fusion protein to the transcription activating fusion protein occurs to a lesser extent in the presence of the test composition than in its absence, i.e., if the presence or increased concentration of the test composition reduces the concentration of two-hybrid complex, then the test composition is or contains a phosphopeptide binding pair inhibitor. The presence or absence of two-hybrid complex may be monitored by measuring the the level of expression of the reporter gene.

To recap, an illustrative in vivo assay format relies upon genetically engineered cells capable of expressing a reporter gene under PBP-mediated transcriptional control. These cells contain a phosphopeptide binding domain of interest and a corresponding peptide ligand, each in the form of a distinct fusion protein. Each such fusion protein thus comprises, among other component regions, at least one PBD or peptide ligand sequence. The two fusion protein are designed to be capable of forming a complex with each other through binding of the tyrosine-phosphorylated ligand domain of one fusion protein to the PBD of the other fusion protein. In the presence of a kinase activity capable of tyrosine-phosphorylating the ligand domain, as discussed elsewhere, and in hormone-dependent embodiments, in the presence of the necessary hormone, the cells express the reporter gene unless an inhibitory substance is present which interferes with the formation or persistence of the two-hybrid complex required for transcription of the reporter gene. In this assay, the cells are cultured or maintained in a suitable culture medium to establish a base-line for expression of the reporter gene. The test composition is added to the culture medium and the ability of the test composition to inhibit expression of the reporter gene is measured. A series of experiments with different concentrations of the test compositions can be conducted in parallel. If the level of reporter gene expression is reduced in the presence of the test composition, the test composition is an inhibitor. If the structure of the inhibitor so identified is not yet known, the compound may then be isolated from the other assay components and characterized. It may be re-evaluated, if desired, using engineered cells expressing analogous fusion proteins but bearing different PBDs and/or peptide ligand domains. This provides a means to confirm the selectivity of the interaction of the inhibitor with the PBP which it was identified. If desired, the binding affinity of the inhibitor for the PBD or peptide ligand domain with which it was identified may be determined, e.g. such as through the use of BIAcoreE technology. The inhibitor so identified may be assayed in an in vitro binding assay as described above and may further be evaluated for pharmacological and/or toxicological activity in various in vitro and/or in vivo assays, as desired.

A wide variety of test compositions can be assayed in accordance with this invention, including, e.g., microbial broths, cellular extracts, conditioned media from cell lines or from host cells transformed with genetic libraries, collections of synthetic compounds, combinatorial libraries or other compounds or mixtures from synthetic programs based on conventional medicinal chemistry approaches or structure-based drug design.

This invention thus provides a means for identifying selective inhibitors of phosphopeptide binding interactions. As noted at the outset, phosphopeptide binding domains are present in a wide variety of proteins, including proteins involved in intracellular signal transduction pathways relevant to a number of important normal and disease processes. Accordingly, inhibitors identified through this invention may be useful for a variety of purposes. First, they may be useful as biological reagents in assays as described herein for functional classification of a phosphopeptide domain or phosphopeptide receptor of a particular protein, particularly a newly discovered protein. Families or classes of such proteins may thus be defined functionally, with respect to binding specificity.

Moreover, inhibitory agents of this invention can be used to inhibit the occurrence of biological events resulting from molecular interactions mediated by a phosphopeptide binding domain. This invention thus provides a method and reagents for inhibiting (totally or partially) the interaction between a protein containing a phosphopeptide binding domain and a natural ligand thereto (i.e., a protein which normally binds in a cell to the SH2, PID or other phosphopeptide binding protein) or a biological activity mediated by such interaction. In a research context, such inhibition can be used to study the biological role of the signaling event and the cell and molecular biology of the affected signal transduction pathway.

An inhibitor identified by the method of this invention can be formulated into a pharmaceutical composition containing a pharmaceutically acceptable carrier and/or other excipient (s) using conventional materials and means. Such a composition can be administered to an animal, either human or non-human, for prevention or treatment of a disease or condition resulting from cellular events involving a phosphopeptide/PBD-mediated protein-protein interaction. Administration of such composition may be by any conventional route (parenteral, oral, inhalation, and the like) using appropriate formulations as are well known in this art. The inhibitor of this invention can be employed in admixture with conventional excipients, i.e., pharmaceutically acceptable organic or inorganic carrier substances suitable for parenteral administration. Inhibitors first identified by these methods, pharmaceutical compositions containing such inhibitors, and pharmaceutical methods involving administration of such inhibitors to patients for the treatment or prevention of diseases mediated by the binding interactions of naturally occurring phosphopeptide binding pairs is therefore an important object of this invention.

Other aspects and advantages of the present invention are described further in the following detailed description of the preferred embodiments thereof.

DETAILED DESCRIPTION OF THE INVENTION

Figure 1:
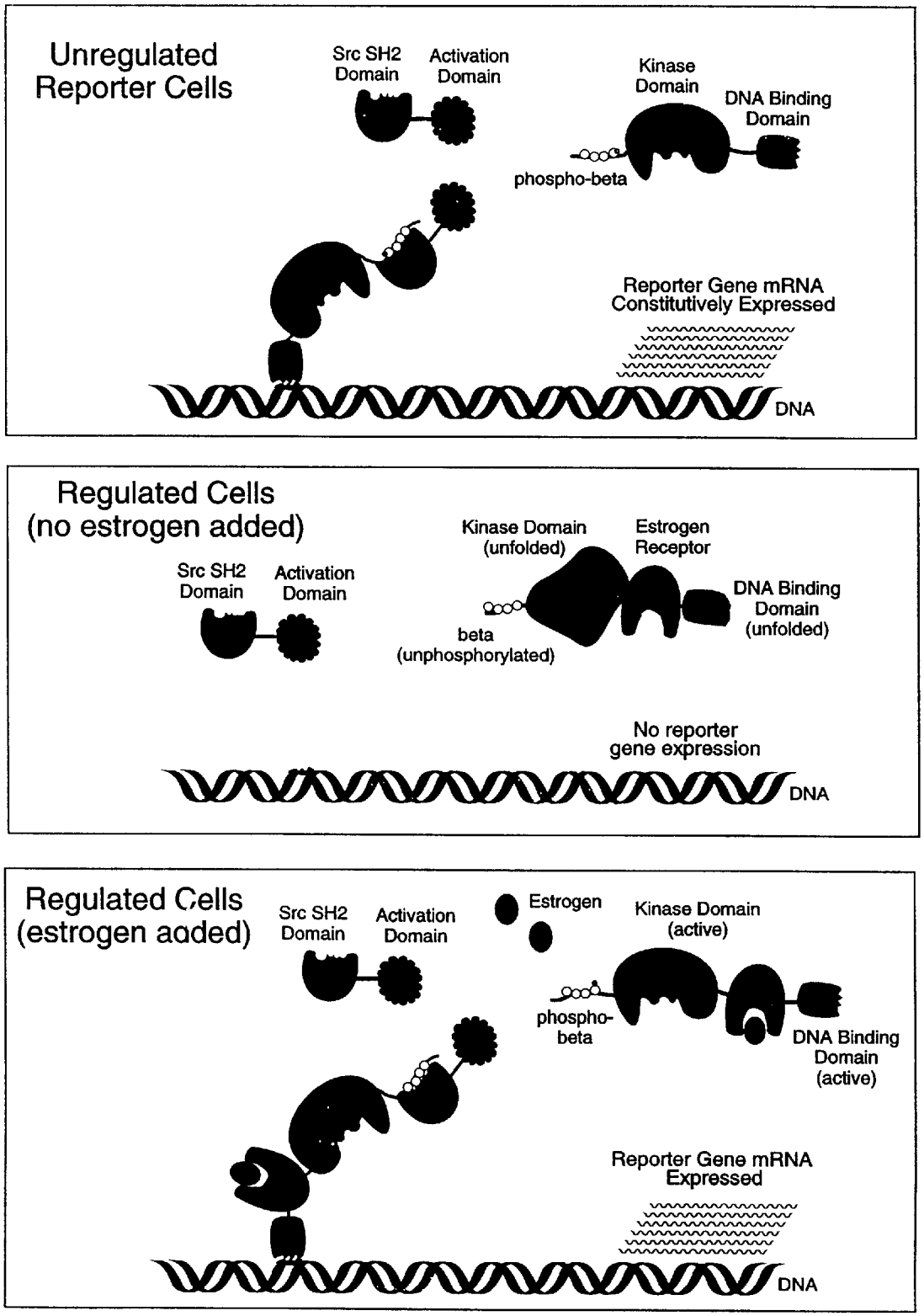
FIG. 1 depicts various assay configurations of this invention.

The present invention addresses current needs in the art of drug discovery by providing a mechanism-based, cellular two-hybrid assay for identifying inhibitors of key molecules involved in certain signal transduction pathways. This assay permits the determination of whether a test or unknown compound is capable of blocking a specific phosphopeptide-mediated association, and provides compositions and methods for identifying and functionally characterizing such inhibitors. This invention permits the identification of inhibitors of the molecular association between an SH2, PID or other phosphopeptide binding domain of a given protein and a naturally occurring ligand therefor. The inhibitors so identified are themselves useful in therapeutic and pharmaceutical compositions and regimens.

Among other features, this invention provides genetically engineered cells, preferably eucaryotic cells, useful for high throughput identification of compounds which interfere with, inhibit or otherwise impede interactions mediated by the binding of a tyrosine-phosphorylated ligand with its phosphopeptide binding protein. The cells of this invention contain and are capable of expressing a reporter gene and genes encoding two fusion proteins. One of the fusion proteins contains a phosphopeptide binding domain, the other contains a ligand for that PBD. The two fusion proteins are capable of binding to each other and when they do so, of detectably activating the transcription of the reporter gene.

One or both of the fusion proteins may also contain one or more optional domains or elements, including a domain capable of regulatabiy sequestering the fusion protein at a desired cellular location or compartment or in an inactive conformation.

In the practice of this invention, cells containing the components mentioned above are cultured under suitable conditions and in a suitable culture medium permitting cell growth and a detectable level of expression of the reporter gene. A test substance is added to the medium, the cells are cultured for an appropriate incubation period, i.e. permitting an inhibitor to enter cells, block two-hybrid formation or persistence and effect a detectable change in reporter gene expression. The level of expression of the reporter gene is then measured. A decrease in the level of expression of the reporter gene indicates that the test substance is a candidate inhibitor.

The assay may be repeated using a control cell containing the reporter gene and its associated control elements and further containing and being capable of expressing a gene encoding a transcription factor fusion protein as a positive control. The transcription factor fusion protein contains both a DNA binding domain and a transcriptional activating domain permitting it to actuate transcription of the reporter gene. The DBD and TAD are typically the same domains which are separately present in the respective DNA-binding and transcriptional activating fusion proteins, previously described. Alternatively, the control cell may express in place of the transcription factor fusion protein, two alternative two-hybrid fusion proteins which were designed based on a different protein binding pair than the phosphopeptide binding pair represented by by the primary two-hybrid assay cells as described above. The failure of the test substance to significantly alter the level of expression of the reporter gene in such controls supports the conclusion that the test substance is not generally inhibiting the assay or inhibiting the assay read-out via an irrelevant mechanism. Such controls help confirm the phosphopeptide binding inhibitor status of candidate inhibitors.

I. Definitions

To facilitate understanding of this invention, the following definitions are provided:

A "peptide ligand" as used herein defines a polypeptide motif or fragment thereof which contains one or more tyrosine residues, and which is capable of binding to a phosphopeptide binding domain such as an SH2 or PID domain when at least one of the peptide ligand's tyrosine residues is phosphorylated. A peptide ligand may be an oligopeptide, polypeptide or protein fragment or portion. (The terms "polypeptide" and "protein" are used interchangeably herein.)

A "phosphopeptide binding domain" (PBD) is an amino acid sequence or poiypeptide region, typically present in certain signaling proteins, which is capable of selective and specific binding to a characteristic tyrosine-phosphorylated ligand. The binding of a tyrosine-phosphorylated ligand to a PBD is considered to mediate or direct the association of the proteins and the transduction of the intracellular signal.

A "phosphopeptide binding pair" (PBP) consists of a PBD and a peptide ligand therefor.

An "SH2 domain" is an example of a PBD. An "SH2 ligand" is an example of a peptide ligand.

A "phosphopeptide binding pair inhibitor" is a compound which can be shown to to inhibit the formation or persistance of binding between a PBD and a tyrosine-phosphorylated peptide ligand therefor. A phosphopeptide binding pair inhibitor may function by binding to a PBD with competitive avidity vis-a-vis a tyrosine-phosphorylated peptide ligand for the PBD, binding to a tyrosine-phosphoryiated peptide ligand for the PBD with competitive avidity vis-a-vis the PBD, or otherwise disrupting the normal binding between a PBD and a tyrosine-phosphorylated peptide ligand.

A "DNA Binding Domain" (DBD) is a polypeptide or protein domain, e.g. a portion of a transcription factor, which binds to a DNA sequence, typically a transcription regulatory DNA element linked to a target or reporter gene.

A "Transcription Activator Domain" (TAD) is a polypeptide or protein domain, e.g. a portion of a transcription factor, which when in proximity to transcription regulatory DNA elements of a target gene, activates gene transcription (and is typically linked to a nuclear localization sequence).

A "reporter gene" is a gene which upon expression, produces a detectable gene product.

The term "DNA element" is used to refer to transcription regulatory DNA sequence, typically upstream of a target or reporter gene, which binds to the DBD and permits transcription in the presence of an appropriate transcription factor or two-hybrid complex.

A "DNA binding fusion protein" is a fusion protein composed of at least one copy of a DBD fused to at least one copy of a member of a PBP. A "Transcription activator fusion protein" is a fusion protein composed of at least one copy of a TAD fused to at least one copy of the other member of a PBP.

II. The Engineered Cells of the Invention

A. The Host Cells

Any eukaryotic cells which can be transformed with heterologous DNA and which can be grown or maintained in culture may be used to prepare the novel engineered cells of this invention. However, mammalian cells are presently preferred. Mammalian cells include, without limitation, those of mouse, hamster, rat, rabbit, dog, cow or primate, including human, origin. They may be of a wide variety of tissue types, including without limitation, mast cells, fibroblasts, osteoclasts, osteoblasts, macrophages, neutrophils, other T cells, epithelial cells, endothelial cells, hepatic cells, kidney cells, or other cell types and may be primary cells or cell lines.

Yeast cells may also be used as the host eukaryotic cells of this invention.

The host cells of this invention are engineered by the introduction therein of heterologous DNA(s) encoding and capable of directing the expression of the fusion proteins as well as heterologous DNA comprising a reporter gene under the transcription control of a DNA element responsive to the "two-hybrid" complex of the DNA-binding fusion protein with the transcription activator fusion protein.

The DNA molecule(s) encoding the two fusion proteins, as well as DNA comprising the reporter gene and its associated DNA element, may be introduced into the host cells as separate DNAs or as one or more DNAs linked together.

B. Reporter Gene Constructs

Suitable reporter genes include any gene whose expression can be detected. Many such genes are known to the art, including, without limitation, those encoding an enzyme which catalyzes a reaction resulting in a detectable color change, an enzyme that permits continued cell growth or viability in the presence of an otherwise toxic agent or absence of an otherwise essential nutrient, a repressor or suppressor of a biological function which is activated or enhanced by the reduced expression of the "reporter" gene or simply a gene product which can be conveniently detected.

Examples of reporter genes which may be used in the practice of this invention include, without limitation, genes encoding enzymes such as luciferase, beta-galactosidase, alkaline phosphatase and horseradish peroxidase. The proteins encoded by these genes catalyze reactions generating readily detectable products. Alternatively, the reporter gene may encode a readily detectable cell surface marker such as Thy1 or a secreted protein such as hGH for which there is a convenient, and preferably commercially available, assay. One well known reporter gene, which is exemplified herein, is the gene encoding secreted alkaline phosphatase (SEAP). [Berger, J., et al., Gene, 66:1–10 (1988)]

The production of SEAP may be monitored from the culture media without the need to lyse the cells. This permits convenient detection, using a conventional calorimetric or fluorescent assay, at different time points during the assays of the invention.

The reporter gene is linked to a DNA element recognized by the DBD and permitting gene expression in response to two hybrid formation (i.e., complexation of the first and second fusion proteins). The DNA element may comprise a synthetic promoter sequence consisting of multiple DBD binding sites upstream of a TATA box element. The number of such binding sites can be adjusted to optimize the overall level of reporter gene expression induced by the fusion proteins of this invention. Examples of such binding sites include GAL4 binding sites [see e.g. Acheson, "DNA Tumor Viruses", Cold Spring Harbor, N.Y., (Tooze, J. ed., 1980) pp 151–160; Peden et al, Science, 209:1392–1396 (1980); Liu & Green, Cell, 61:1217–1224 (1990); and Ptashne & Gann, Nature, 346:329–331 (1990)].

The DNA element of the reporter gene, when introduced into cells, will preferably not be occupied in the absence of exogenously added DBD of the second fusion protein. The extent of occupancy of the DNA element may be determined by measuring the level of reporter gene transcription in the absence and presence of the the fusion proteins, the kinase domain or the transcription factor fusion protein.

By way of illustration, one particular embodiment of the invention uses a reporter gene construct containing DNA encoding SEAP linked to a DNA element containing iterated GAL4 binding sites. Additional guidance in the use of suitable promoters for this reporter gene may be obtained from Fields et al, U.S. Pat. No. 5,283,173 (Feb. 1, 1994) and Vasavada et al, Proc. Natl. Acad. Sci., USA, 88:10686–10690 (1991).

C Fusion Protein Constructs

The two fusion proteins of this invention typically contain either (a) one or more DNA binding domains ("DBDs", which may be the same or different), or (b) one or more transcription activation domains ("TADs", which may be the same or different), in addition to one or more phosphopeptide binding domains or peptide ligands therefor. For instance, in one embodiment, the first fusion protein has an SH2 domain or a tandem SH2 region (two SH2 domains) and a transcription activation domain, while the second fusion protein has a DNA binding domain and an SH2 ligand domain, capable after tyrosine phosphorylation, of binding with the SH2 domain(s):

1st fusion protein: SH2 domain-TAD 2d fusion protein: DBD-SH2 ligand

In preferred embodiments, the second fusion protein contains a hormone ligand binding domain and a protein tyrosine kinase domain linking the DBD and SH2 ligand domain, as discussed in further detail below.

The DBD and the TAD of the two fusion proteins typically originate from a transcription factor. The DBDs and TADs may be derived from the same or different transcription factors and may be optimized by genetic engineering. DBDs and TADs are often derived from transcription factors having separable DNA-binding and transcription activation domains.

i. Transcription Factors

A large number of transcription factors are known which require two subunits for activity, that is, a single transcription factor can be divided into two separate functional domains (e.g. a TAD and a DBD). While each domain is inactive (transcriptionally) by itself, the paired components, when in close proximity, comprise an active transcription factor.

Transcription factors which can be used in this invention include yeast GAL4, which can be divided into two domains [Ma and Ptashne, Cell, 48: 847–853 (1987) and U.S. Pat. No. 5,283,173]. One may use, for instance, a fusion of GAL4(1-147)-SNF1 and SNF4-GAL4(768-881), where the SNF1 and GAL4 may be replaced by the subject binding proteins as binding domains. Combinations of GAL4 and VP16 or HNF-1 and VP16 can be employed. Each of these proteins will have a linked partner, part of an interacting pair. The interaction (binding partner recognition) will bring the TAD (VP16) to DNA (GAL4 or HNF-1) and transcription will be induced. Other transcription factors that may be used for the method of this invention include, but are not restricted to, the members of the Jun, Fos, and ATF/CREB families, Oct1, Sp1, HNF-3, the steroid receptor superfamily, and the like. Other TADs and DBDs which may be used in the practice of this invention are well known in the art.

The transcription factor can be endogenous or exogenous with respect to the desired host cells. If the transcription factors are exogenous, but functional within the host and can cooperate with the endogenous RNA polymerase (rather than requiring an exogenous RNA polymerase, for which a gene could be introduced), then an exogenous promoter element functional with the DBDs or TADs of the transcription factor can be provided with another construct for regulating transcription of the reporter gene. Thus, the initiation of transcription can be restricted to the gene(s) associated with the exogenous promoter region, i.e., the reporter gene(s).

ii. DNA Binding Domains

DNA-binding domains for use in this invention may be selected from a wide variety of DNA-binding domains known in the art. Examples include DNA-binding domains of the homeodomain class, the zinc-finger class, and the paired-box class, for which numerous examples are known in the literature. In cases where detailed information on the molecular contacts of the protein with DNA is available, the DNA recognition specificity of the protein may be engineered by amino acid substitutions.

A preferred feature for DNA binding domains is the lack of interactions with other cellular proteins. Alternatively, the nature of such interactions should be known with precision, so that these interactions can be abrogated by suitable amino acid substitutions within the DNA-binding domain. In addition, the DNA binding domain will preferably be unique for the cell type utilized. The DNA binding element, when introduced into cells, will preferably not be occupied (at least not unduly) in the absence of exogenously added DNA binding domain. The level of background occupancy may be determined through appropriate controls as discussed previously.

Cell-type specific factors (not found in the cells used for the in vivo assay), DNA binding domains with altered binding specificity and procaryotic DNA binding domains are well suited for the methods described. One suitable DNA-binding domain is derived from the Phox1 protein (Grueneberg, D. A., Natesan, S., Alexandre, C. and Gilman, M. Z. (1992). Human and Drosophila homeodomain protein the enhance the DNA-binding activity of serum response factor. Science 257, 1089–1095: Genbank accession number: M95929). This protein is a member of the homeodomain class. A 69 amino-acid domain derived from Phox1 is sufficient to bind DNA. High-affinity DNA recognition sequences for the protein have also been identified, as have amino acid substitutions that change its DNA recognition specificity and that affect its ability to interact with certain endogenous proteins in human cells. (Grueneberg et al)

A second suitable DNA-binding domain is derived from the SRE-ZBP protein (Attar, R. M. and Gilman, M. Z. (1992). Expression cloning of a novel zinc-finger protein that binds to the c-fos serum response element. Mol.Cell. Biol. 12, 2432–2443; Genbank accession number: M88579). SRE-ZBP is a member of the C2H2 class of zinc-finger proteins. It has seven tandem zinc fingers. Any one of these zinc-finger domains or any combination of two or more domains can be used to generate a DNA-binding domain with novel recognition specificity. Furthermore, because the general structure and mode of DNA recognition is known for proteins of this class, DNA recognition can be directly modified if necessary.

A third suitable DNA-binding domain is the GAL4 binding domain referred to previously.

A fourth suitable type of DNA-binding domain is a composite DNA binding domain as described in published International Patent Application No. WO 96/20951 and exemplified by ZFHD1. See also Pomeranz et al. 1995, Science 267:93–96.

iii. Transcription Activation Domains

Preferred transcription activation domains are compact in size, potent in activity, and nontoxic to cells. Additional features become relevant for particular applications. For example, for constructs to be used in one particular type of cell or tissue, activator domains with especially high activity in the host cell are used. In applications that involve the stable integration of the target gene into host cell DNA, activator domains that resist chromatin suppression are used.

Numerous activation domains are known in the art. Two illustrative activation domains which may be used in the practice of this invention are the VP16 activation domain and the NF-kB p65 activation domain. See e.g. International Patent Application Nos. WO 96/20951 and WO 96141865.

iv. Phosphopeptide Binding Pairs

Each of the fusion proteins contains either at least one TAD or at least one DBD linked to at least one member of a PBP, i.e. to at least one phophopeptide binding domain or peptide ligand therefor. One exemplary PBP is an SH2 domain and a peptide ligand therefor (e.g., a ZAP SH2 domain and an immunoreceptor activation motif such as the TCR zeta ITAM). As noted previously, the ligand domain will contain one or more Tyr residues, which must be phosphorylated to bind to the SH2 domain. By way of further example, the peptide ligand domain may be an IgE ITAM, the polyoma middle T phosphorylation sequence or a synthetic consensus tyrosine phosphoryiation binding site.

In some embodiments, inclusion of protein domains that are not generally regarded as influencing, either allosterically or otherwise, the behavior of the SH2 or PID or other such domain may be included to stabilize the folding, enhance expression or provide a means of identifying or manipulating the protein (e.g. fusion to glutathione-S-transferase or other domains that aid in identification/purification, epitope tags, etc).

As illustrated below, the fusion proteins may contain a plurality of PBDs or ligands therefore. For example, one embodiment of the present invention uses a fusion protein containing a tandem SH2 domain from ZAP-70 (containing two SH2 domains).

Peptide ligand(s) members of the PBP for use in the fusion proteins are defined above. For example, where one member of a binding pair member is an SH2 domain, the other member, i.e., the peptide ligand, may be a naturally occurring ITAM containing at least one Tyr. Peptide ligands in their nonphosphorylated state will not bind the PBDs. These ligands must be phosphorylated by endogenous or (introduced) hetterologous protein tyrosine kinase activity within the cell.

A large number of SH2 domains, PIDs, and other phosphopeptide binding domains, as well as ligands therefor, are known in the art and may be adapted for use in this invention. The following additional background information and guidance may be of interest and use to the practitioner.

Identification of SH2 or SH2-like Domains

The term "SH2-like domain or a subdomain thereof" refers to a sequence which is substantially homologous to a Src homology region 2 (SH2 region), or a subdomain of an SH region preferably a conserved region of an SH region. The Src homology region is a noncatalytic domain of –100 amino acids which was originally identified in the viral Fps and viral Src cytoplasmic tyrosine kinases by virtue of its effects on both catalytic activity and substrate phosphorylation (T. Pawson, Oncogene 3, 491 (1988) and 1. Sadowski et al., Mol. Cell. Biol. 6, 4396 (1986)). SH2 domains have been found in a variety of eukaryotic proteins, some of which function in intracellular signal transduction. Many are known inthe art. Examples (including counterparts from various species) of SH2 domain-containing proteins include (1) members of the src-family protein tyrosine kinases (Src, Lyn, Fyn, Lck, Hck, Fgr, Yes), (2) Shc (3) Tsk, (4) Btk, (5) VAV, (6) Grb2, (7) Crk, and (8) signal transducer and transcription (STAT) proteins. In addition, a number of proteins, such as ZAP-70, p85 phosphatidylinositol 3' kinase (Pl3K), Syk, GTPase Activating Protein (GAP), and Phospholipase C gamma, have two SH2 domains. SH2 domain-containing proteins have been identified in human, rodent, sheep, bovine, C. elegans, Drosophila, Xenopus, flatworm, freshwater sponge, and hydra.

One way to identify new SH2 or SH2-like domains from unknown DNA, RNA or protein sequence is by using one of many available computer alignment programs. One example is pfscan, which can be run via the World Wide Web (WWW) site at http:Hluirec3.unil.ch/software/profilescan.html. To use the program, a protein sequence is tested against a "profile" describing the SH2 domain motif. According to the program information, the particular strength of profiles is that they can be used to describe very divergent protein motifs. These profiles are normally derived from multiple alignments of the initial sequence set. In addition to the sequences themselves, a profile identifies which types of residues are allowed at what position within the domain, which amino acids are conserved, which ones are not, which positions or regions can allow insertions, and which regions may be dispensable. Additional information on Pfscan and PROSITE can be obtained at the web page http:/iuirec3.unil.ch/index.html operated by the Bioinformatics Group at the ISREC (Swiss Institute for Experimental Cancer Research).

As an example we analyzed the peptide sequence of human Src with the pfscan program. The results are shown below. The program clearly identified the SH2 domain of Src as encompassing the region from amino acids 150–247 of the Src peptide sequence. In addition, the SH3 and kinase domains were identified by pfscan.

NScore raw from-to Profile | Description 26.9695 1792 pos. 150–247 PS50001 | SH2 Src homology 2 (SH2) domain 20.2947 1182 pos. 83–144 PS50002 | SH3 Src homology 3 (SH3) domain 43.4246 2912 pos. 269–522 PS50011 | PROTEIN_KINASE_DOM Protein kinase The NScore of a match is the negative decadic logarithm of the expected number of matches of the given quality (or better) in a random database of the given size. For NScores <<1 this converges to the probability of finding the match in the database. Since the number of expected matches depends on the size of the database, the decadic logarithm of the database size must be subtracted before the calculation:

$$-\log(NExp) = NScore - \log(DBsize)$$

where (NExp=Expected number of chance matches) and (DBsize=size of the database in characters).

The following table gives somes examples on how to convert the NScores into probabilities for the SwissProt database and the nonredundant (nr) protein database. The calculation is based on a database size of 18,531,385 residues for SwissProt (log=7.27)

58,154,119 residues for the nr database (log=7.76)

| | Expected chance matches in: | |
|---|---|---|
| NScore | SwissProt | nonredundant |
| 7.0 | 1.8 | 5.8 |
| 7.5 | 0.58 | 1.82 |
| 8.0 | 0.18 | 0.58 |
| 8.5 | 0.058 | 0.182 |
| 9.0 | 0.018 | 0.058 |
| 9.5 | 0.006 | 0.0182 |
| 10.0 | 0.0018 | 0.0058 |
| 10.5 | 0.0006 | 0.0018 |
| . . . and so on . . . | | |

The segment of a test sequence contains an SH2 domain with an SH2 profile NScore value >7.5, preferably >8, more preferably >9, more preferably >10.

As a second example, the N-terminal 160 amino acid sequence from human ZAP-70 was applied to pfscan. The result indicated an SH2 domain bounded by amino acids 10–102.

| NScore | raw | from-to | Profile | | Description |
|---|---|---|---|---|---|
| 16.4402 | 1082 | pos. 10–102 | PS50001 | | SH2 Src homology 2 (SH2) domain |

The minimal segment encoding an SH2 or SH2-like domain as determined by sequence alignment may not be enough to function or function optimally in the assay. Additional sequences either N-terminal and/or C-terminal of this minimal segment may be necessary or desirable for optimizing the binding of the encoded protein to a peptide ligand within the context of the invention. These additional sequences may be derived from the natural protein sequence or may be derived from other proteins or even non-natural sequences that are added to the expression vector. However, the sequence required can be readily determined biochemically, in an in vitro binding assay, or genetically, using the production of SEAP as an indicator of SH2 domain-phosphopeptide interaction.

SH2 domains can be identified using other computer alignment programs, such as MegAlign within the DNAstar computer package (Madison, Wis.). To do this, one or more known SH2 domains and a test sequence are aligned by the clustal method. A sequence having >25%, in some cases 30–50%, in other cases >50%, amino acids identical to a known SH2 domain is identified as an SH2 homology domain. The positions of identical amino acids between the test sequence and different known SH2 domains can vary, except for one position. All SH2 domains identified to date have a conserved arginine residue approximately 25–40 residues from the start of the SH2 homology domain. In human src this arginine is found within the sequence FLVRES, where abbreviations for the amino acid residues are: F, Phe; L, Leu; V, Val; R, Arg; E, Glu; S, Ser.

Another way to identify SH2 or SH2-like domains is by running a query in the federated nucleotide or protein databases for the SH2 domain feature. In the SWISS-PROT database, this is listed under the FT or "feature" heading. SWISS-PROT database can be accessed over the WWW at EBI http://www.ebi.ac.uk. For example, in the file listed for human Src (P12931), the region containing the SH2 domain is shown to be 150–247.

| SWISS-PROT: P12931 | | | | |
|---|---|---|---|---|
| ID | SRC_HUMAN | STANDARD; | PRT; | 535 AA. |
| AC | P12931; | | | |
| DR | MIM; 190090; -. | | | |
| DR | PROSITE; PS00107; PROTEIN_KINASE_ATP. | | | |
| DR | PROSITE; PS00109; PROTEIN_KINASE_TYR. | | | |
| DR | PROSITE; PS50001; SH2. | | | |
| DR | PROSITE; PS50002; SH3. | | | |
| DR | PROSITE; PS50011; PROTEIN_KINASE_DOM. | | | |
| DR | PRODOM [Domain structure / List ot seq. sharing at least 1 domain] | | | |
| DR | SWISS-2DPAGE; GET REGION ON 2D PAGE. | | | |
| KW | TRANSFERASE; TYROSINE-PROTEIN KINASE; PROTO-ONCOGENE; PHOSPHORYLATION; | | | |
| KW | ATP-BINDING; MYRISTYLATION; SH3 DOMAIN; SH2 DOMAIN. | | | |
| FT | INIT_MET | 0 | 0 | BY SIMILARITY. |
| FT | LIPID | 1 | 1 | MYRISTATE (BY SIMILARITY). |
| FT | DOMAIN | 83 | 144 | SH3. |
| FT | DOMAIN | 150 | 247 | SH2. |
| FT | DOMAIN | 269 | 522 | PROTEIN KINASE. |
| FT | NP_BIND | 275 | 283 | ATP (BY SIMILARITY). |

-continued

| SWISS-PROT: P12931 | | | | |
|---|---|---|---|---|
| FT | BINDING | 297 | 297 | ATP (BY SIMILARITY). |
| FT | ACT_SITE | 388 | 388 | BY SIMILARITY. |
| FT | MOD_RES | 419 | 419 | PHOSPHORYLATION (AUTO-) (BY SIMILARITY). |
| FT | MOD_RES | 529 | 529 | PHOSPHORYLATLON (BY SIMILARITY). |

Yet another way to identify SH2 or SH2-like domains may be accomplished by screening a cDNA expression library with a phosphorylated peptide ligand for a known SH2 domain to isolate cDNAs for SH2 proteins. One could use PCR or low stringency screening with an SH2-specific probe. The SH2 domain or protein containing the SH2 domain may be isolated from naturally occuring sources (e.g. cells, tissues, organs, etc); produced recombinantly in bacteria, yeast or eukaryotic cells; produced in vitro using cell free translation systems; or produced synthetically (e.g. peptide synthesis).

identify a particular protein sequence as an SH2-like domain.

The alignment of SH2 domains used to generate the SH2 profile for pfscan, as taken from http://ulrec3.unil.ch/prf_details/alignments/SH2.msf (profile matrix can be obtained from http://ulrec3.unil.ch/cgi-bin/get_pstprf?SH2) is based on alignment of approximately 390 SH2 domains from proteins of various species. The list of proteins containing SH2 domains used in the alignments in the Swiss-Prot Database includes the following (P##### is the Swiss-Prot Database Accession number):

| | | | | | |
|---|---|---|---|---|---|
| P00519, | ABL1_HUMAN | P00520, | ABL_MOUSE | P00521, | ABL_MLVAB |
| P00522, | ABL_DROME | P00523, | SRC_CHICK | P00524, | SRC_RSVSR |
| P00525, | SRC_AVISR | P00526, | SRC_RSVP | P00527, | YES_AVISY |
| P00528, | SRC1_DROME | P00530, | FPS_FUJSV | P00541, | FPS_AVISP |
| P00542, | FES_FSVGA | P00543, | FES_FSVST | P00544, | FGR_FSVGR |
| P03949, | ABL1_CAEEL | P05433, | GAGC_AVISC | P05480, | SRCN_MOUSE |
| P06239, | LCK_HUMAN | P06240, | LCK_MOUSE | P06241, | FYN_HUMAN |
| P07332, | FES_HUMAN | P07947, | YES_HUMAN | P07948, | LYN_HUMAN |
| P08103, | HCK_MOUSE | P08487, | PIP4_BOVIN | P08630, | SRC2_DROME |
| P08631, | HCK_HUMAN | P09324, | YES_CHICK | P09769, | FGR_HUMAN |
| P09851, | GTPA_BOVIN | P10447, | ABL_FSVHY | P10686, | PIP4_RAT |
| P10936, | YES_XENLA | P12931, | SRC_HUMAN | P13115, | SRC1_XENLA |
| P13116, | SRC2_XENLA | P13406, | FYN_XENLA | P14084, | SRC_AVISS |
| P14085, | SRC_AVIST | P14234, | FGR_MOUSE | P14238, | FES_FELCA |
| P15054, | SRC_AVIS2 | P15498, | VAV_HUMAN | P16277, | BLK_MOUSE |
| P16333, | NCK_HUMAN | P16591, | FER_HUMAN | P16879, | FES_MOUSE |
| P16885, | PIP5_HUMAN | P17713, | STK_HYDAT | P18106, | FPS_DROME |
| P19174, | PIP4_HUMAN | P20936, | GTPA_HUMAN | P23615, | SPT6_YEAST |
| P23726, | P85B_BOVIN | P23727, | P85A_BOVIN | P24135, | PIP5_RAT |
| P24604, | TEC_MOUSE | P25020, | SRC_RSVH1 | P25911, | LYN_MOUSE |
| P26450, | P85A_MOUSE | P27446, | FYN_XIPHE | P27447, | YES_XIPHE |
| P27870, | VAV_MOUSE | P27986, | P85A_HUMAN | P29349, | CSW_DROME |
| P29350, | PTN6_HUMAN | P29351, | PTN6_MOUSE | P29353, | SHC_HUMAN |
| P29354, | GRB2_HUMAN | P29355, | SEM5_CAEEL | P31693, | SRC_RSVPA |
| P32577, | CSK_RAT | P34265, | YKF1_CAEEL | P35235, | PTNB_MOUSE |
| P35991, | BTK_MOUSE | P39688, | FYN_MOUSE | P40763, | STA3_HUMAN |
| P41239, | CSK_CHICK | P41240, | CSK_HUMAN | P41241, | CSK_MOUSE |
| P41242, | CTK_MOUSE | P41243, | CTK_RAT | P41499, | PTNB_RAT |
| P42224, | STA1_HUMAN | P42225, | STA1_MOUSE | P42226, | STA2_HUMAN |
| P42227, | STA3_MOUSE | P42228, | STA4_MOUSE | P42229, | STA5_HUMAN |
| P42230, | STA5_MOUSE | P42231, | STA5_SHEEP | P42232, | STAB_MOUSE |
| P42679, | CTK_HUMAN | P42680, | TEC_HUMAN | P42681, | TXK_HUMAN |
| P42682, | TXK_MOUSE | P42683, | LCK_CHICK | P42684, | ABL2_HUMAN |
| P42685, | FRK_HUMAN | P42686, | SRK1_SPOLA | P42687, | SPK1_DUGTI |
| P42688, | SRK2_SPOLA | P42689, | SRK3_SPOLA | P42690, | SRK4_SPOLA |
| P43403, | ZA70_HUMAN | P43404, | ZA70_MOUSE | P43405, | SYK_HUMAN |
| P46108, | CRK_HUMAN | P46109, | CRKL_HUMAN | Q00655, | SYK_PIG |
| Q02977, | YRK_CHICK | Q03526, | ITK_MOUSE | Q04205, | TENS_CHICK |
| Q04736, | YES_MOUSE | Q04929, | CRK_CHICK | Q05876, | FYN_CHICK |
| Q06124, | PTNB_HUMAN | Q06187, | BTK_HUMAN | Q07014, | LYN_RAT |
| Q07883, | GRB2_CHICK | Q08012, | DRK_DROME | Q08881, | ITK_HUMAN |

Certain SH2 or SH2-like domains may not be identified via the pfscan program nor exhibit significant homology with known SH2 domain sequences to be detected by computer alignment programs. These sequences may, nevertheless, exhibit the same or similar three-dimensional structure as known SH2 domains and function as an SH2-like domain and function to bind phosphotyrosine-containing peptides or proteins. The three-dimensional structure of several known SH2 domains have been determined. SH2 domains are characterized as two anti-parallel beta sheets composed of 5 or 6 beta strands. Regions forming an alpha helix may or may not be present within the domain. SH2 or SH2-like domains may be recognized as having an SH2-like domain structure when solved by x-ray crystallography or NMR spectroscopy. Alternatively, a predicted structure by homology modeling may be used to A general method to identify an SH2 domain within a test peptide or nucleotide sequence follows:
1. Translate the cDNA or RNA into single letter code protein sequence. This could be accomplished using a computer program such as DNA strider or EditSeq in the DNAstar package.
2. Go to the WWW site at http://ulrec3.unil.ch/software/profilescan.html
3. Copy the test sequence into the appropriate box in the pfscan form
4. Submit the form to the ptscan server
5. The results are sent back through the web browser or via e-mail.

The subject invention is relevant to SH2 and SH2-like domains as described in the foregoing paragraphs. Using information provided herein, and by analogy to the examples provided below, one may carry out this invention with any SH2 domain, SH2-like domain, PID or PID-like domain and a peptide ligand therefor, e.g. in place of ZAP, Syk, Src or Fyn SH2 domains.

Identification of PID or PID-like Domains

An alternative phosphotyrosine binding domain to SH2 domains is the so-called phosphotyrosine interaction domain (PID). This domain, containing on average about 160 amino acid residues, was originally identified in the Shc protein. In contrast to SH2 domains, which recognize sequences having a consensus pTyr-Xaa-Xaa-Xaa-Xaa (a phosphotyrosine followed by three or more amino acids), PID domains recognize sequences with the consensus Asn-Xaa-Pro-pTyr (also called NPXY in single letter code). The invention described in this application is also relevant to PID and PID-like domains. In this case, the coding sequence for a PID domain is substituted in the appropriate vector for the SH2 domain coding sequence and a ligand that recognizes the PID domain replaces the SH2 domain ligand. Phosphorylation of the PID ligand could be accomplished using v-Src, as described herein. Alternative protein kinases could be used to phosphorylate the PID ligand. In addition, a protein kinase endogenous within the cell could catalyze phosphorylation of the PID ligand.

Significant information concerning these domains is known in the art. A detailed description of the PID domains can also be found on the WWW at the site http://twww.bork.embl-heidelberg.de/Modules/pid-gif.html. The following information is taken from that site:

Documentation—PROSITE Description

Beside SH2, the phosphotyrosine interaction domain (PI domain or PID)[3] is the second phosphotyrosine-binding domain found in the transforming protein Shc [1,2]. Shc couples activated growth factor receptors to a signalling pathway that regulates the proliferation of mammalian cells and it might participate in the transforming activity of oncogenic tyrosine kinases. The PI domain specifically binds to the Asn-Pro-Xaa-Tyr(p) motif found in many tyrosine-phosphorylated proteins including growth factor receptors. PID has also been found in the Shc related protein Sck [1] and several otherwise unrelated regulatory proteins [3] which are listed below.

Mammalian Shc (46 kD and 52 kD isoforms) contains one N-terminal PID, a collagen-like domain and a C-terminal SH2 domain.

Human Shc related protein Sck contains one PI domain and a SH2 domain.

Mammalian X11 is expressed prominently in the nervous system. It contains 2 disc homologous regions (DHR) of about 100 AA downstream of the PID.

Drosophila nuclear Numb protein is required in determination of cell fate during sensory organ formation in drosophila embryos. It has one PID.

Caenorhabditis hypothetical protein F56D2.1 contains an N-terminal metalloproteinase domain followed by one PID.

Rat FE65. The WW domain as well as the 2 PIDs found in the sequence of FE65 indicate that this protein is probably involved in signal transduction.

Drosophila protein disabled is a cytoplasmic, tyrosine phosphorylated protein found in CNS axons and body wall muscles. It is involved in embryonic neural development. It contains one N-terminal PI domain.

Mouse mitogen responsive phosphoprotein isoformns P96, P93 and P67 which are produced by alternative splicing, contain one N-terminal PID. This is also true for the differentially expressed human ortholog Doc-2.

Human EST05045 protein fragment has one PID.

References:

[1] Kavanaugh W. M., Williams L. T. Science 266:1862–1865(1994)

[2] Blaiki, P. et al., J.Biol.Chem. 269, 32031–32034 (1994)

[3] Bork P., Margolis B. Cell 80, 693 (1995)

A PI domain alignment based on approximately 40 PI domains from various species is illustrated in the WWW site at http:Hluirec3.unil.ch/prf_details/alignments/PID.msf. An alignment based on approximately 50 PID sequences is shown at the web site at http://www.bork.embl-heidelberg.de/Modules/pi-ali.html.

The minimal segment encoding a PID or PID-like domain as determined by sequence alignment may not be enough to function or function optimally in the assay. Additional sequences either N-terminal and/or C-terminal of this minimal segment may be necessary or desirable for optimizing the binding of the encoded protein to a peptide ligand within the context of the invention. These additional sequences may be derived from the natural protein sequence or may be derived from other proteins or even non-natural sequences that are added to the expression vector. However, the sequence required can be determined biochemically, in an in vitro binding assay, or genetically, using the production of SEAP as an indicator of PID domain-phosphopeptide interaction.

v. Optional Domains

One or both of the fusion proteins may also contain one or more optional domains, including a protein kinase domain, as mentioned above, or a domain capable of regulatably rendering the fusion protein unavailable for 2-hybrid formation (e.g. by sequestering the fusion protein at a desired cellular location or compartment or by maintaining the fusion protein in an inactive conformation).

Kinase Domains. As one example, if the cell does not have an endogenous protein kinase capable of phosphorylating the tyrosine residues of the peptide ligand for the SH2, PID or other phosphopeptide binding domain, a heterologous kinase activity is introduced into the cell. A DNA encoding such a heterologous kinase may be introduced into the cell as an independent transcription unit (i.e., with its own transcription regulatory elements, such as a promoter and/or enhancer sequence). Alternatively, a kinase activity may be introduced as a functional kinase domain within one of the two fusion proteins of this invention. In one embodiment the fusion proteins comprise a first chimera containing one or more SH2 domains linked to one or more transcription activation domains and a second chimera containing a DBD-kinase domain-peptide ligand domain fusion.

In one embodiment, the protein kinase domain from the v-Src protein was used to phosphorylate the peptide ligand linked to the DNA binding domain. Alternative protein kinases may be used to conduct this phosphorylation. The recognition of protein kinase domains can be conducted by the same approaches described for SH2 or PID domains using pfscan, ClustalV analysis, hybridization, or functional biochemical analysis. A segment defining the protein kinase homology region is approximately 280 amino acids. A detailed alignment of protein kinase domains can be obtained at the pfscan web site listed above or at the protein kinase web site at University of California at San Diego (http://www.sdsc.edu/kinases/). The minimal segment encoding a protein kinase domain as determined by sequence alignment is bounded by a conserved glycine in the N-terminal portion and a conserved arginine at the C-terminal portion. However, additional sequences either N-terminal and/or C-terminal of this minimal segment may be necessary or desirable for the encoded protein to functionally phosphorylate the peptide ligand within the context of the invention. These additional sequences may be derived from the natural protein kinase sequence or may be derived from other proteins or even non-natural sequences that are added to the expression vector. The sequence required can be readily determined biochemically, in an in vitro phosphorylation reaction, or genetically, using the production of SEAP as an indicator of SH2 (or PID) domain-phosphopeptide interaction. For domains that recognize phosphothreonine or phosphoserine-modified peptides, an appropriate protein kinase would be substituted for the v-Src kinase domain.

Localization domains. As another example, fusion proteins of this invention may also contain a targeting sequence providing for translocation of the protein to the nucleus. Such a targeting sequence may have a plurality of basic amino acids, referred to as a bipartite basic repeat [see, e.g., Garcia-Bustos et al, *Biochem. Biophys. Acta*, 1071:83–101 (1991)]. This sequence can appear in any portion of the molecule internal or proximal to the N- or C-terminus and results in localization of the fusion protein within the nucleus.

Nuclear Hormone Binding Domains. Compounds introduced into cells may be labile and therefore not present for long periods of time once introduced into the cell. In such cases, it would be advantageous to have all components present in the cell at the time the cells are exposed to test compositions. We therefore have made constructs encoding fusion proteins containing a nuclear hormone ligand binding domain (HBD). Numerous such hormone receptors and ligands are known which may be used in the practice of this invention, including estrogen, glucocorticoid, retinoic acid, aldosterone and vitamin D receptors. The regulatory properties of a nuclear hormone ligand binding domain (Picard et al, Cell (1988) 54, 1073–1080; Eilers et al, Nature (1989) 340, 66–68) allow the post-translational regulation of interaction of the fusion proteins. By way of illustration, an estrogen receptor domain serves as an autonomous regulatory domain: upon fusion to a heterologous protein, the steroid receptor domain subjects the chimeric protein to hormonal control. This regulatory property is due to the hormone-reversable interactions of the HBD with heat shock proteins. For example, a PBD-TAD fusion protein and a DBD-HBD-kinase-PBD ligand fusion protein can be expressed in cells containing the reporter gene construct. Only with the addition of steroid hormone will the fusion proteins be able to interact. In the absence of hormone, the HBD-containing fusion protein will not be competent to interact with its complementary fusion protein to form the two-hybrid complex.

Other domains that may optionally be included within the fusion proteins include an antibody recognition sequence (epitope tag) permitting detection using antibodies. Such monitoring can be useful to confirm that the fusion protein is made and that the level of expression is not affected by compounds tested for inhibition of phosphopeptide domain binding.

III. Assembly of Fusion Protein Constructs, Reporter Gene Plasmids and Genetically Engineered Cells of the Invention Constructs encoding the fusion proteins and containing the reporter genes of this invention can be introduced into the cells as one or more DNA molecules or constructs, in many cases in association with one or more markers to allow for selection of host cells which contain the construct(s). The constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. For example, a DNA sequence encoding the DNA-binding domain or TAD(s) is joined to DNA encoding the appropriate member of the PBP. These sequences are joined such that they constitute a single open reading frame that can be translated in cells into a single polypeptide harboring all intended domains. The order and arrangement of the domains within the polypeptide can vary. The construct(s) once completed and demonstrated to have the appropriate sequences may then be introduced into a host cell by any convenient or desired means. The constructs may be incorporated into vectors capable of episomal replication (e.g. BPV or EBV vectors) or into vectors designed for integration into the host cells' chromosomes. The constructs may be integrated and packaged into non-replicating, defective viral genomes like Adenovirus, Adeno-associated virus (AAV), or Herpes simplex virus (HSV) or others, including retroviral vectors, for infection or transduction into cells. Alternatively, the construct may be introduced by protoplast fusion, electroporation, biolistics, calcium phosphate transfection, lipofection, microinjection of DNA or the like. The host cells will in some cases be grown and expanded in culture before introduction of the construct(s), followed by the appropriate treatment for introduction of the construct(s) and integration of the construct(s). It may be most convenient to use simple transfection procedures. The cells will then be expanded and screened by virtue of a marker present in the constructs. Various markers which may be used successfully include hprt, neomycin resistance, thymidine kinase, hygromycin resistance, etc., and various cell-surface markers such as Tac, CD8, CD3, Thy1 and the NGF receptor.

In some instances, one may have a target site for homologous recombination, where it is desired that a construct be integrated at a particular locus. For example, one can delete and/or replace an endogenous gene (at the same locus or elsewhere) with a recombinant target construct of this invention. For homologous recombination, one may generally use either Ω or O-vectors. See, for example, Thomas and Capecchi, Cell (1987) 51, 503–512; Mansour, et al., Nature (1988) 336, 348–352; and Joyner, et al., Nature (1989) 338, 153–156.

The constructs may be introduced as a single DNA molecule containing all of the genes, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in procaryotes or eucaryotes, and mammalian expression control elements, etc. which may be used to prepare stocks of construct DNAs and for carrying out transfections are well known in the art, and many are commercially available.

Additional background information and general guidance to the practitioner with respect to design, assembly, incorporation into plasmids, and transfection of constructs for such fusion proteins and reporter genes is available in the following published international patent applciations: WO 94/18317, WO 95/02684, WO 96/20951, WO 95/24419 and WO 96/41865, the contents of which are incorporated herein by reference.

IV. The Assay Method of the Invention

Genetically engineered cells containing the various DNA constructs described above may be used to carry out the assay method of this invention. Such assays permit one to identify the presence in a test composition of an inhibitor of the binding of a PBP with a tyrosine-phosphorylated ligand therefore. Test compositions or compounds to be assessed for their inhibitory activity can be obtained from a variety of sources, including, for example, microbial broths, cellular extracts, conditioned media from cells, synthetic compounds and combinatorial libraries, and may be tested individually or in pools. The assay method of this invention may be used to screen natural product and test compound libraries or structurally-biased diversity libraries to identify desired inhibitors. The test composition may be selected from a mixture of one or more test peptides, wherein said mixture is provided in the form of a library of synthetic peptides or in the form of a phage library displaying the various peptides.

A. The General Method

The method involves the use of a cell as described above, particularly a cell in which the second fusion protein also contains a heterologous kinase domain or the cell contains an endogenous or heterologous kinase capable of tyrosine-phosphorylating the ligand domain. According to this method, the above-described engineered cells are cultured or maintained in a conventional culture medium under suitable conditions permitting growth of the cells both in the presence and absence of the test composition. For example, the cell is cultured in standard tissue culture media containing the drugs necessary to select for cells which stably retain the introduced genes described above. Cells may be cultured in standard tissue culture dishes, e.g. multidishes and microwell plates, or in other vessels or arrays of vessels, as desired.

The test compounds are added to the culture media to assay their effect on PBP interaction. Cells at this time may be bathed in tissue culture media (with or without serum) or a balanced salt solution. The compounds to be tested may be cell permeable and therefore added directly to cells. Alternatively, it may be necessary to first make the cells permeable using streptolysin O, tetanolysin or another cell permeabilizing agent.

During incubation and growth of the cells in the absence of an inhibitor test composition, the cell is capable of expressing the above recited fusion proteins and receptor gene product. Normally this involves the DNA-binding fusion protein binding to the DNA element of the receptor gene. Tyrosine residues in the peptide ligand domain are phosphorylated by the kinase activity (endogenous or heterologous) in the cell The phosphorylated peptide ligand, e.g., an ITAM, binds its PBD on the other fusion protein, e.g., an SH2 domain [see, e.g., Pawson, U.S. Pat. No. 5,352,660 (Oct. 4, 1994)] to generate the two-hybrid complex. The end result is measurable expression of the detectable reporter gene product.

Thus, an additional step of this method is determining whether production of the detectable gene product was diminished in the presence of the test composition. After transcription is induced, cells or media are evaluated to measure reporter gene expression. In some configurations, the assay is conducted in 96 well plates or other arrays, and the reporter gene expression is measured in situ. In other cases, cells or media are harvested and an extract prepared (if necessary) for evaluation. Comparison of the measurements of detectable reporter gene product in the presence and absence of the test composition permits the identification of the test composition as an inhibitor of the PBP interaction. Transcription of the detectable gene product induced due to PBP interactions is assayed using standard calorimetric or fluorescence assays.

For example, if the test compound is not an inhibitor of the formation and/or stability of the PBP complex, the measurement of detectable reporter gene product in the presence and absence of the text composition will be about equivalent, since the results of a noninhibitor will be similar to results obtained with no test compound, as described above. If the test compound is a putative inhibitor of the PBP interaction, a decrease in the level reporter gene expression is observed. This decrease indicates that test compound inhibited the binding of the PBD to its phosphorylated peptide ligand, and thus inhibited the formatio or persistence of the two-hybrid complex. The receptor gene expression is thus extinguished or reduced, depending on the amount of test composition present in the culture and the strength of the binding between the test compound and either member of the PBP.

For example, in one embodiment of this invention, test compounds are screened in eukaryotic host cells for blocking/inhibiting the interaction between the ZAP-70 tandem SH2 domain with the TCR zeta ITAM in vivo (see Example 3). Compounds that block ZAP SH2 binding to ITAM sequence are detected using a first fusion protein comprising the vSrc kinase domain, estrogen receptor domain, and the TCR zeta ITAM ligand fused to a DNA-binding domain and a second fusion protein comprising the tandem SH2 domain of ZAP fused to a TAD. The interaction of the ZAP SH2 domains with the zeta ITAM domain brings the activator domain in proximity to the DNA element, inducing reporter gene transcription. Compounds that block ZAP SH2-zeta ITAM interaction reduce reporter gene expression.

In this embodiment, and by way of illustration, the assay method of this invention offers several advantages over traditional T cell assays. The assay readout is directly dependent on the interaction between the particular SH2 ligand and the SH2 domain-containing polypeptide (e.g., the ZAP-70 tandem SH2 domain). In contrast, in standard T cell assays that measure cell proliferation, cytolytic activity or cytokine production, there are many steps between activation and the assay endpoints. Therefore, many nonspecific inhibitors score in standard T cell assays, which will not score in the assay of this invention.

B. Eliminating Non-Specific Inhibition

To exclude test compounds that inhibit reporter gene expression by nonspecific mechanisms (e.g., by having a general inhibitory effect on cellular transcription or translation), test compounds are also assayed for their effect on reporter gene expression when reporter gene transcription is not dependent on PBP interactions. For this purpose, an indicator cell line is utilized wherein the transcription activation domain is brought directly to DNA by the DBD (by expressing in cells a DBD/transcription activation domain fusion). To rule out false positives based on otherwise nonrelevant effects of a test composition relating to the HBD, the fusion protein may further contain a hormone binding domain (HBD). In such cases, the only difference between the positive control indicator cell line and the assay cell line is the dependence of the assay cell line upon PBP complex formation for reporter gene expression.

General inhibitory effects of transcription are also revealed by performing radiolabeled uridine pulse labelings during exposure to the test compound. Inhibition of general incorporation of radiolabel indicates a general inhibitory effect on transcription.

C Simultaneous Exposure of the Cell to the Assay Components

In another aspect of this method, the first fusion protein transfected into the cell contains an HBD, as described above. The HBD is an important feature of this aspect of the method of use of this cell. Test compounds introduced into cells may be labile and therefore not present for long periods of time once introduced into the cell. It would be advantageous to have all interacting components present in the cell at the time the cells are exposed to potential inhibitors of the PBP interaction.

Inhibitors of phosphopeptide binding protein-protein interactions could exert their effect in two ways. They could compete with the ligand/HBD/TAD domain for the PBD or displace the ligand/HBD/TAD, which has complexed with the PBD. Mechanistically, it will be easier to block than displace the interaction between the binding domain and its ligand Potential inhibitors, i.e., test compounds, can be introduced into cells prior to complex formation (hormone addition) to block complex formation.

D. Ceal-Free Assay

In another embodiment of this method, cell-free transcription systems prepared from cells as described above or prepared from the purified components described above may be used in lieu of the engineered cells. In a cell free implementation, peptide ligands may be synthetic or non-synthetic peptides, peptoids or small molecules identified from libraries, cell broths, natural extracts, etc. The method of the assay is the same as above, except that it is performed in a cell free environment. In this case, the kinase domain should preferably be part of the fusion protein containing the DBD and the ligand domain for the phosphopeptide binding domain.

V. The Identified Phosphopeptide Binding Pair Inhibitors

A PBP inhibitor identified by the methods of this invention selectively binds to a PBD of interest, such as SH2 domain. Such an inhibitor can block or inhibit protein-protein, protein-peptide, protein-nucleotide, protein-polynucieotide, protein-lipid, protein-carbohydrate or protein-small molecule interactions mediated by a phosphopeptide binding domain of interest.

Once an agent has been identified as an phosphopeptide binding or blocking/inhibiting agent, it can be produced using known methods, such as by recombinant methods of protein production or chemical synthesis. It can also be obtained from the source in which it was initially identified.

A. Counterscreens

Having identified a PBP inhibitor by means of the above assay, rapid and high throughput counterscreens using cells expressing a monomeric transcription factor (i.e. a positive control fusion protein containing one or more copies of both the DBD and TAD) that drives reporter gene expression independent of a protein kinase can readily identify non-specific inhibitors, or confirm inhibitor specificity. Test compounds identified as inhibitors by the method of this invention may be further evaluated for binding activity with respect to one or more additional PBDs of interest, or with respect to additional proteins containing the domain(s), using various approaches, a number of which are well known in the art.

The counterscreen assays may include all of the core features of the above-described general assay of this invention, but the fusion proteins are altered to determine whether the inhibitor binds to other ligands, or other domains. The readout is independent of the particular PBD peptide and peptide ligand used in the original screen. Such counterscreens may be repeated as described to obtain the specificity. Therefore, any nonspecific inhibitors (e.g., RNA transcription, protein synthesis) can be identified.

For instance, such identified inhibitors may be evaluated for activity as competitive inhibitors of the binding of an SH2 domain with a phosphorylated ligand thereto [e.g. Pawson, U.S. Pat. No. 5,352,660 (Oct. 4, 1994)]. As another example, the counterscreen assay may use a control cell containing and capable of expressing the reporter gene and its associated control elements and a gene encoding a control fusion protein. The control fusion protein contains both the DBD and the TAD which are separately present in the respective DNA binding and transcription activator fusion proteins, previously described. Alternatively, two fusion proteins may be used, each containing one half of a binding partner with different binding specificities than those found for PBD and the protein-protein interaction assayed as described above. The failure of the test compound to significantly alter the level of expression of the reporter gene confirms its activity as an inhibitor.

Another counterscreen assay useful in evaluating test compounds shown to be inhibitors by the method of this invention for binding to one or more additional PBDs of interest is surface plasmon resonance (BIAcore®) technology [see, e.g., Panayotou et al, *Mol. Cell. Biol.*, 13: 3567–3576 (1993)].

In another counterscreen, a plasmid that drives the expression of a nuclear located tyrosine phosphatase, linked to the estrogen receptor ligand binding domain can be introduced into the cells. A number of proteins have had their function Tendered steroid hormone-dependent by fusion to the steroid hormone receptor ligand binding domain. The hormone binding domain of steroid hormone receptors acts as a molecular switch. In the absence of cognate ligand, the fusion protein is inactive. However, hormone binding leads to the very rapid (within seconds or minutes) "gain of function" of the chimeric protein. Heterologous proteins made hormone-dependent for function include both enzymes and transcription factors. Thus, with the addition of estrogen, detectable protein production would be curtailed, due to the dephosphorylation of the peptide ligand. Such cells could be used to screen for phosphatase inhibitors that block the reduction of reporter production that would occur when the cells are exposed to estrogen.

In a further possible counterscreen, compounds may be tested in an assay as described herein, but replacing the PBD and peptide ligand domains with SH3 and SH3 ligand domains as described in WO95/24419. Compounds should not be active unless they inhibit a non PBP-related component of the assay system or also inhibit SH3-mediated protein-protein interactions.

The inhibitors identified in the assay system of this invention can be further evaluated by conventional methods for possible therapeutic applications, toxicological and pharmacological activity. For example, test compounds so identified as inhibitors may further be evaluated for activity in inhibiting cellular or other biological events mediated by a pathway involving the PBD-based interaction of interest using a suitable cell-based assay or an animal model. Cell-based assays and animal models suitable for evaluating inhibitory activity of a test compound with respect to a wide variety of cellular and other biological events are known in the art. New assays and models are regularly developed and reported in the scientific literature.

By way of nonlimiting example, compounds which bind to an SH2 domain involved in the transduction of a signal leading to asthma or allergic episodes may be evaluated in a mast cell or basophil degranulation assay. The inhibitory activity of a test compound identified as an SH2 inhibitor by the method of this invention with respect to cellular release of specific mediators such as histamine, leukotrienes, hormonal mediators and/or cytokines, as well as its biological activity with respect to the levels of phosphatidylinositol hydrolysis or tyrosine phosphorylation can be characterized with conventional in vitro assays as an indication of biological activity. [See, e.g., Edward L. Barsumian et al, *Eur. J. Immunol.*, 11:317–323 (1981); M. J. Forrest, *Biochem. Pharmacol.*, 42:1221–1228 (1991) (measuring N-acetyl-betaglucosaminadase from activated neutrophils); and V. M. Stephan et al., *J. Biol. Chem.*, 267:5434–5441 (1992)].

For example, histamine release can be measured by a radioimmunoassay using a kit available from AMAC Inc. (Westbrook, Me.). One can thus evaluate the biological activity of inhibitors identified by the method of this invention and compare them to one another and to known active compounds or clinically relevant compounds which can be used as positive controls.

Generally speaking, in such assays IC50 scores of 150–300 uM are considered of interest, scores of 50–150 uM are considered good, and scores below about 50 uM are of high interest. Prior to in vivo models, inhibitors identified by this invention may also be tested in an ex vivo assay for their ability to block antigen-stimulated contraction of sensitized guinea pig tracheal strip tissue. Activity in this assay has been shown to be useful in predicting the efficacy of potential anti-asthma drugs.

Numerous animal models of asthma have been developed and can be used [for reviews, see Larson, "Experimental Models of Reversible Airway Obstruction", in THE LUNG, Scientific Foundations, Crystal, West et al. (eds.), Raven Press, New York, pp. 953–965 (1991); Warner et al., *Am. Rev. Respir. Dis.*, 141:253–257 (1990)]. Species used in animal models of asthma include mice, rats, guinea pigs, rabbits, dogs, sheep and primates. Other in vivo models available are described in Cross et al., *Lab Invest.*, 63:162–170 (1990); and Koh, et al., *Science*, 5:1210–1213 (1992).

By way of further example, compounds identified as PBP inhibitors by the method of this invention which bind to an PBD involved in the transduction of a signal involved in the initiation, maintenance or spread of cancerous growth may be evaluated in relevant conventional in vitro and in vivo assays. See e.g., Ishii et al., *J. Antibiot.*, XLII:1877–1878 (1989); and U.S. Pat. No. 5,206,249 (issued Apr. 27, 1993).

VI. Uses of Inhibitors Identified by This Invention

Inhibitors identified by this invention may be used as biological reagents in assays as described herein for functional classification of a PBD of a particular protein, particularly a newly discovered protein. Families or classes of PBD-bearing proteins may now be defined functionally, with respect to ligand specificity. Moreover, inhibitors identified by this invention can be used to inhibit the occurrence of biological events resulting from molecular interactions mediated by a PBP. Inhibiting such interactions can be useful in research aimed at better understanding the biology of PBP-mediated events.

Such binding or blocking agents would be useful, for example, in the diagnosis, prevention or treatment of conditions or diseases resulting from a cellular processes mediated by a PBP interaction. For example, a patient can be treated to prevent the occurrence or progression of osteoporosis or to reverse its course by administering to the patient in need thereof an SH2 binding or blocking agent which selectively binds Src SH2.

There are many other conditions for which phosphopeptide binding or blocking agents may be useful therapeutically, including, e.g., breast cancer where the SH2 domain-containing proteins Src, PLCgamma and Grb7 have been implicated. Other relevant conditions include prostate cancer, in which case targeting Grb2, PLCg, and P13K, all of which contain SH2 domains, may be useful in treatment or prevention of the disease. Inhibition of the interaction of Grb2 or Abl SH2 domains with Bcr-abl may be useful to treat chronic myelogenous leukemia (CML) or acute myelogenous leukemia (AML).

Still other relevant applications of an PBP inhibitor would be to prevent interferon-, growth factor-, or cytokine-mediated diseases (e.g. inflammatory diseases) by targeting the PBDs of STAT proteins. Agents that block the SH2 domains of ZAP-70, which is believed to be involved in activation of T-cells, would be useful in the treatment of autoimmune diseases. An inhibitor that blocks one or both SH2 domains of ZAP-70 would also be useful as an immunosuppressant to prevent rejection of skin and organ transplants.

By virtue of the capacity to inhibit protein-protein interactions required for cellular events of pharmacologic importance, PBD/peptide ligand interaction inhibitors identified by the method may be used in pharmaceutical compositions and methods for treatment or prevention in a subject in need thereof. Such inhibitors can be used to treat or prevent the diseases or their pathological effects mediated by such interactions.

For example, drugs that completely block one of the two ZAP SH2 domains should effectively prevent ZAP from associating with the activated TCR and thus block T cell activation. A ZAP antagonist or inhibitor would specifically inhibit T cells and avoid the toxicity of the currently used immunosuppressive drugs, FK506 and cyclosporin, which target the more ubiquitously expressed protein, calcineurin. Since calcineurin is required for cellular activities in several tissues in addition to T cells, cyclosporin and FK506 cause side effects in the kidney and central nervous system which limit their application largely to patients with organ transplant rejection.

VII. Pharmaceutical Compositions and Methods

A. Compositions

Inhibitors identified by this invention can be formulated into pharmaceutical compositions containing a therapeutically (or prophylactically) effective amount of the inhibitor in admixture with a pharmaceutically acceptable carrier and/or other excipients (i.e., pharmaceutically acceptable organic or inorganic carrier substances suitable for parenteral administration) using conventional materials and means. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Topical compositions include a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils. Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary.

Materials and methods for producing the various formulations are well known in the art [see e.g. U.S. Pat. Nos. 5,182,293 and 4,837,311].

B. Methods

The invention provides methods of treating, preventing and/or alleviating the symptoms and/or severity of a disease or disorder referred to above by administration to a subject of a PBP inhibitor in an amount effective therefor. The subject will be an animal, including but not limited to animals such as cows, pigs, chickens, etc., and is preferably a mammal, and most preferably human. By "mammals" is meant rodents such as mice, rats and guinea pigs as well as dogs, cats, horses, cattle, sheep, nonhuman primates and humans. Such effective amounts can be readily determined by evaluating the inhibitors identified by this invention in conventional assays well-known in the art, including assays described herein.

Administration of such composition may be by any conventional route using appropriate formulations as are well known in this art. Various delivery systems are known and can be used to administer the inhibitor, e.g., encapsulation in liposomes, microparticles, microcapsules. One mode of delivery of interest is via pulmonary administration. Other methods of introduction include but are not limited to intradermal, intramuscular, intraperitoneal, intravenous, subcutaneous, intranasal, epidural, nasal and oral routes. The inhibitor may be administered by infusion or bolus injection, by absorption through epithelial or mucocutaneous linings (e.g., oral mucosa, rectal and intestinal mucosa, etc.) and may be administered together with other biologically active agents.

Administration can be systemic or local. For treatment or prophylaxis of nasal, bronchial or pulmonary conditions, preferred routes of administration are oral, nasal or via a bronchial aerosol or nebulizer. In specific embodiments, it may thus be desirable to administer the inhibitor locally to the area in need of treatment; this may be achieved by, for example, and not by way of limitation, local infusion during surgery, topical application, by injection, by means of a catheter, by means of a suppository, or by means of a skin patch or implant, said implant being of a porous, nonporous, or gelatinous material, including membranes, such as sialastic membranes, or fibers.

Administration to an individual of an effective amount of the inhibitor can also be accomplished topically by administering the compound(s) directly to the affected area of the skin of the individual. In certain instances, it is expected that the inhibitor may be disposed within devices placed upon, in, or under the skin. Such devices include patches, implants, and injections which release the compound into the skin, by either passive or active release mechanisms.

The amount of the inhibitor which will be effective in the treatment or prevention of a particular disorder or condition will depend on the nature of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. For example, a typical effective dose of the inhibitor is in the range of about 0.01 to about 50 mg/kgs, preferably about 0.1 to about 10 mg/kg of mammalian body weight, administered in single or multiple doses. Generally, the inhibitor may be administered to patients in need of such treatment in a daily dose range of about 1 to about 2000 mg per patient.

The precise dosage level of the inhibitor, as the active component(s), should be determined by the attending physician or other health care provider and will depend upon well known factors, including the phosphopeptide binding interaction under consideration, the route of administration, and the age, body weight, sex and general health of the individual; the nature, severity and clinical stage of the disease; and the use (or not) of concomitant therapies.

C. Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration.

Other components such as physiologically acceptable surfactants (e.g., glycerides), excipients (e.g., lactose), carriers, and diluents may also be included.

The following examples illustrate various aspects of this invention. These examples do not limit the scope of this invention which is defined by the appended claims.

EXAMPLES

Example 1

Plasmids

A. Plasmid pYSZ, a GAL4 (1-147)-vSrc Kinase-Zeta ITAM Yeast Expression Vector.

Plasmid pGTB9 (Clontech Laboratories) was used for the expression of GAL4 (1-147)-vSrc kinase-Zeta ITAM in yeast. This plasmid has a 2 micron origin of replication and sequences for Amp (bacteria) or Trp (yeast) selection. pGTB9 also has ADH1 regulatory sequences that direct the expression of the GAL4 DBD fusion proteins. Downstream of GAL4 coding sequences are multiple restriction endonuclease cloning sites.

The vSrc gene (Genbank Accession #J02342) kinase domain was introduced downstream of GAL4 sequences in pGTB9 as an EcoRI/BamHI fragment after PCR amplification. The 5' and 3' oligonucleotides, respectively, utilized for PCR were: (EcoRI end) cgGAATTCtccaagccccagaccca [SEO ID NO:1] and (Bam H1 end) gcGGATCCctcagcgactccaaca [SEQ ID NO:2]. These oligos amplify residues 248–526 of vSrc. PCR generated vSrc kinase DNA was sequenced after cloning to check the fidelity of the amplification process.

Sequences encoding human Zeta chain cytoplasmic residues (Genbank Accession# J04132, residues 52–164), cloned into pET23b (invitrogen) were excised using Nde 1 and Hind III. The restriction fragment encoding Zeta residues was blunt ended using T4 DNA polymerase and ligated to blunt ended SalI digested pGTB9-vSrc Kinase DNA. The recombinant DNA was digested with restriction endonucleases to identity a clone which contained Zeta coding sequences in the proper orientation.

B. pYAZ22, a GAL4 Activation Domain-tandem ZAP SH2 Yeast Expression Vector.

Plasmid pGAD424 (Clontech Laboratories) was used for the expression of GAL4 activation domain-tandem ZAP SH2 fusion protein in yeast. pGex2KT-huZAP(1–259), containing residues 1–259 of human ZAP-70 (Genbank Accession # L05148) was digested with BamHI and blunt ended using T4 DNA polymerase. After the addition of EcoRI linkers (New England Biolabs, catalog #1020), nucleotide sequence encoding the tandem SH2 domains of ZAP (residues 1–259) was isolated as an EcoRI fragment and cloned into the EcoRI site of pGAD424.

The recombinant DNA was digested with restriction endonucleases to identity a clone which contained ZAP SH2 domain coding sequences in the proper orientation.

C. pYerSZ, an Estrogen Regulated GAL4 (1-147)-vSrc Kinase-Zeta ITAM Yeast Expression Vector.

Human estrogen receptor ligand binding domain (I.d.b.) coding sequences (residues 282–595) were amplified by PCR from pHuER (Genbank Accession# M12674) using the 5' and 3' oligonucleotide primers, respectively, (EcoRI end) cgGMTrCtctgctggagacatgagagct ISEQ ID NO:3] and (EcoRI end) cgGAAMrCgactgtggcagggaaaccct [SEO ID NO:4]. After digesting the amplified DNA using restriction endonuclease EcoRI, estrogen receptor l.d.b. sequences were cloned into EcoRI cut pYSZ (Example 1A). A recombinant clone was isolated that had estrogen receptor sequences in the right orientation. This new plasmid, pYerSZ, directs the expression of GAL4 DBD-estrogen receptor l.d.b.-vSrc kinase-Zeta ITAM fusion protein in yeast.

D. PMSZ, a GAL4 (1-147)-vSrc Kinase-Zeta ITAM Mammalian Cell Expression Vector.

pBXG1, a pECE72-based vector [Sadowski I. and Ptashne, M., *Nucl. Acids Res.*, 17:7539 (1989)1, was used for the expression of GAL4 DBD fusion proteins in mammalian cells. pECE72 [Ellis, L., et al. Cell, 45:721–732 (1986)] has the SV40 virus origin of replication, SV40 early promoter and SV40 polyadenylation regulatory sequences. GAL4 (1-147) and multiple cloning sites C-terminal to GAL4 coding sequences were obtained from pSKGAL147 [Kakidani, H. and Ptashne, M., *Cell*, 52:161–167 (1988)] as a Hind III/Xbal fragment and inserted into Hind III/Xbal cut pECE72 to generate pBXG1.

The sequences encoding vsrc kinase Zeta ITAM were excised from pYSZ (Example 1A) as an EcoRI/BglII fragment and cloned into EcoRI/BamHI digested pBXG1 to generate plasmid pMSZ, capable of directing the expression of GAL4 (1-147)-vSrc kinase-Zeta ITAM in mammalian cells.

E. pMAZ22, a Herpes Virus VP16 Activation Domain-tandem ZAP SH2 Domain Mammalian Cell Expression Vector.

pMVN1 (Ivan Sadowski, University of British Colombia, Vancouver, CA) was used for the production of transcription activation domain-tandem ZAP SH2 domain fusion proteins in mammalian cells. pMVN 1 contains the SV40 early promoter, HSV TK translational leader sequence, SV40 nuclear localization sequences and VP16 activation domain residues followed by multiple cloning sites for the construction of novel fusion proteins. The sequences encoding the tandem SH2 domains of ZAP (residues 1–259) were excised from pYAZ22 (Example 1B) as an EcoRI fragment and cloned into EcoRI digested pMVN1 in the proper orientation.

F. pMerSZ, a GAL4 (1-147)-estrogen Receptor l.b.d.-vSrc Kinase-Zeta ITAM Mammalian Cell Expression Vector.

Human estrogen receptor l.d.b. coding sequences were prepared as described in 1C above.

After digesting the amplified DNA using EcoRI, estrogen receptor l.b.d. sequences were cloned into EcoRI-cut pMSZ (Example 1D). A recombinant clone was isolated that had estrogen receptor sequences in the right orientation. This new plasmid, pMerSZ, directs the expression of GAL4 DBD-estrogen receptor l.b.d.-vSrc kinase-Zeta ITAM fusion protein in mammalian cells.

G. pYSB, a GAL4 (1-147)-vSrc Kinase-Beta ITAM Yeast Expression Vector.

pGTB9-vSrc Kinase DNA (see Example 1A) was engineered for the production of GAL4 DBD-vSrc kinase-Beta ITAM chain fusion protein production. Beta sequences (Genbank Accession# S21154) were amplified from pCD8-beta [Rivera, V. and Brugge, J., *Mol. Cell. Biol.*, 15:1582–1590 (1995)] using the 5' and 3' oligonucleotides, respectively: (BamHI end) gcGGATCCggagctggggaa-gaactca [SEQ ID NO:5] and (SalI end) acgcGTCGACt-tataaatcaatgggaggag [SEQ ID NO.:6]. The resulting amplified DNA, after digestion with BamHI and SalI, was cloned into BamHI/SalI digested pGTB9-vSrc Kinase.

H. pYerSB, a GAL4 (1-147)-estrogen Receptor l.b.d.-Src Kinase-Beta ITAM Yeast Expression Vector.

The same human estrogen receptor l.b.d. coding sequences were prepared and amplified by PCR as described in 1C above and cloned into EcoRI cut pYSB (Example 1G). A recombinant clone was isolated that had estrogen receptor sequences in the right orientation. This new plasmid, pYerSB, directs the expression of GAL4 DBD-estrogen receptor l.b.d.-vSrc kinase-Beta ITAM fusion protein in yeast.

I. pYAS32, a GAL4 Activation Domain-Src SH3/SH2 Yeast Expression Vector.

pGAD424 (Clonetech Laboratories) was used for the production of transcription activation domain-human Src SH3/SH2 domain fusion proteins in yeast cells. Sequences encoding the Src SH3/SH2 domain (residues 84–249) Tanaka, A. and Fujita, D. J., *Mol. Cell. Biol.* 6:3900–3909 (1986)] were amplified by PCR using the 5' and 3' oligonucleotides, respectively: (EcoRI end) cctcacGAAT-TCggtggagtgaccacctttgtggcc [SEQ ID NO: 7] and (BamHI end) ccactcGGATCCgccggggcacacggtggtgaggc [SEQ ID NO:8]. After restriction endonuclease digestion using EcoRI and BamHI, the PCR product was ligated to EcoRI/BamHI digested pGAD424.

J. pYAS2, a GAL4 Activation Domain-Src SH2 Yeast Expression Vector.

pGAD424 was used for the production of transcription activation domain-human Src SH2 domain fusion proteins in yeast cells. Sequences encoding the Src SH2 domain (residues 144–249) [see, Tanaka, A. and Fujita, D. J. (1986) cited above] were amplified by PCR using the 5' and 3' oligonucleotides, respectively: (EcoRI end) cctcac-GAATrCggcgactccatccaggctgaggag [SEQ ID NO:9] and (BamHI end) ccactcGGATCCgccggggcacacggtggtgaggc [SEQ ID NO:10].

After digestion with EcoRI and BamHI, the PCR fragment was cloned into EcoRI/BamHI digested pGAD424.

K. pMSB, a GAL4 (1-147)-vSrc Kinase-Beta ITAM Chain Mammalian Cell Expression Vector.

pYSB (Example 1G) was cut with restriction endonucleases EcoRI and BglII and the DNA fragment encoding vSrc kinase-Beta ITAM chain residues was isolated and ligated to EcoRI/BamHI digested pBXG1 (Example 1G).

L. pMerSB, a GAL4 (1-147)-estrogen Receptor l.b.d.-vSrc Kinase-Beta ITAM Chain Mammalian cell Expression Vector.

pMSB (Example 1K) was cut with restriction endonuclease EcoRI. An EcoRI DNA fragment containing the human estrogen receptor l.b.d. coding sequences, prepared as described in 1C above, was ligated to EcoRI digested pMSB. A recombinant clone was isolated that had estrogen receptor sequences in the right orientation. This new plasmid, pMerSB, directs the expression of GAL4 DBD-estrogen receptor l.b.d. vSrc kinase-Beta ITAM fusion protein in mammalian cells.

M. pMAS32, a Herpes Virus VP16 Activation Domain-human Src SH3/SH2 Domain Fusion Protein Mammalian Cell Expression Vector.

pMVN 1 (Ivan Sadowski, Univ. B.C., Vancouver, CA) was used for the production of TAD-human Src SH3/SH2 domain fusion proteins in mammalian cells. Sequences encoding the Src SH3/SH2 domain (residues 84–249; see above) were amplified by PCR using the 5' and 3' oligonucleotides, respectively: (EcoRI end) cctcacGAAT-TCggtggagtgaccacctttgtggcc [SEQ ID NO:1 1] and (BamHI end) ccactcGGATCCgccggggcacacggtggtgaggc [SEQ ID NO:12].

After restriction endonuclease digestion using EcoRI and BamHI, the PCR product was ligated to EcoRII/BamHI digested pMVN 1.

N. pMAS2, a Herpes Virus VP16 Activation Domain-human Src SH2 Domain Fusion Protein Mammalian Cell Expression Vector.

Sequences encoding the Src SH2 domain (residues 144–249) [Tanaka et al, supra] were amplified by PCR using the 5' and 3' oligonucleotides, respectively: (EcoRI end) cctcacGAATTCggcgactccatccaggctgaggag [SEQ ID NO:13] and (BamHI end) ccactcGGATCCgccggggracacg-gtggaggc [SEQ ID NO:14].

After digestion with EcoRI and BamHI, the PCR fragment was cloned into EcoRI/BamHI digested pMVN1 (Example 1M).

O. pMerVP, a GAL4 DBD-estrogen Receptor l.b.d.-VP 16 TAD Fusion Protein Mammalian Cell Expression Vector.

An EcoRI DNA fragment containing the human estrogen receptor l.b.d. coding sequences prepared as described in 1C above was ligated to EcoRI digested pBXGI (Example 1G). Clones containing the estrogen receptor sequences in the right orientation (designated pMer) were identified by restriction endonucleases analysis. VP16 TAD residues were amplified using template plasmid pMVN1 (Example 1M) and the 5' and 3' oligonucleotides, respectively: (BamHI end) cgGGATCCagcctgggggacgagctc [SEQ ID NO:15] and (SpeI end) ggACTAGTcccaccgtactcgtcaat [SEQ ID NO:16]. After digestion with BamHI and SpeI, the PCR fragment was cloned into BamHI/SpeI digested pMer.

P. pMAF2, a Herpes Virus VP16 Activation Domain-human Fyn SH2 Domain Fusion Protein Mammalian Cell Expression Vector.

Sequences encoding the Fyn SH2 domain (residues 149–251) [Genbank M14333] were amplified by PCR using the 5' and 3' oligonucleotides such that the Fyn SH2 domain coding sequences contained EcoRI and BamHI ends. After digestion with EcoRI and BamHI, the PCR fragment was cloned into EcoRI/BamHI digested pMVN1 (Example 1M).

Example 2

Stable Mammalian Cell Line

A variety of cell lines were established by introducing selected plasmid DNA, described in Example 1 into mammalian cells using lipofectin reagent (Gibco BRL) as suggested by the manufacturer.

A selected host cell line is the mammalian HT 1080 fibrosarcoma cell line [American Type Culture Collection Accession No. CRL7951]. These cells are prepared by lipofection using a SEAP reporter construct comprising (a) a GAL4 responsive/dependent promoter (5 GAL4 binding sites linked to the core IL-2 promoter, the "G5-IL2" promoter), which is placed upstream of (b) secreted alkaline phosphatase (SEAP) coding sequences; and a plasmid containing the hygromycin gene.

This cell line G5-IL2 HT1080 was employed in a variety of the examples below.

Example 3

Two-Hybrid Mechanism-Based In Vivo Assay—
Zeta ITAM-Tandem Zap SH2-Dependent Two-
Hybrid Formation in Mammalian Cells In a prototypic example of an assay of this invention, a two hybrid interaction recapitulates a critical event that occurs during T-cell activation, namely the SH2 domain-dependent binding of the ZAP-70 tyrosine kinase to the TCR zeta ITAM chain of the T-cell receptor.

The G5-IL2 HT1080 fibrosarcoma cell line of Example 2 is transfected with two effector plasmids by lipofection:

1) pMSZ (Example 1D) directs the expression of a novel fusion protein that consists of GAL4 DBD residues, the vSrc kinase domain and the human zITAM chain. This fusion protein should bind to DNA and have tyrosine kinase activity. The clustering of these molecules, localized at the G5-IL2 promoter, should help promote efficient zITAM phosphorylation.

2) pMAZ22 (Example 1E) drives the expression of the tandem SH2 domains of ZAP, fused to the herpes virus VP16 TAD.

For use as controls and comparisons, HT1080 cells were also transtected with carrier DNA only, or pMSZ only, or pMS (GAL4 DBD-vSrc kinase), or pMS and pMAZ22.

The transfected host cells are cultured in 6 well dishes. Forty-eight hours after transfection, the amount of SEAP released into the media was determined using a fluorescence assay [J. Berger et al, Gene, 6:1–10 (1988)]. The extent of two-hybrid formation (i.e. the effect on transcription and the amount of ZAP SH2-z ITAM interaction) is ascertained by measuring the amount (i.e., the activity) of the SEAP reporter gene released into the media.

Figure 2:
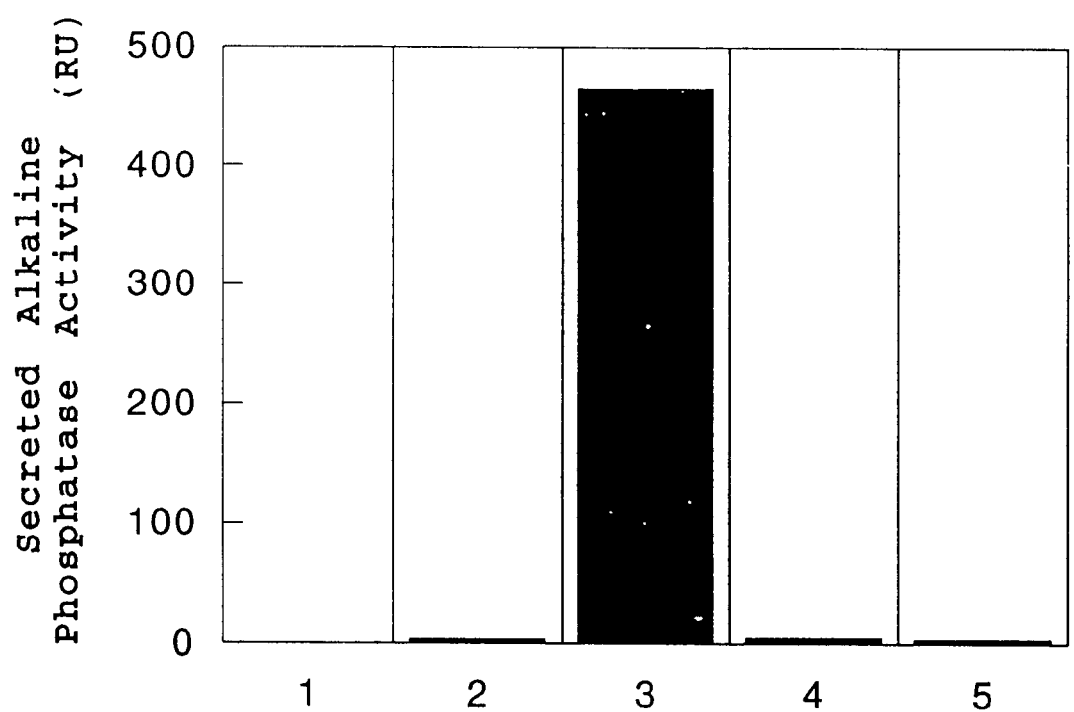
FIG. 2 is a bar graph depicting the results of a zeta (a) ITAM-tandem ZAP SH2-dependent two-hybrid formation in mammalian cells. Secreted alkaline phosphatase (SEAP) activity (RU) is plotted against cells which received the following DNAs, which correspond to the columns in the graph: (1) carrier DNA, (2) pMSZ (Example 1D), (3) pMSZ and pMAZ22 (Example 1E), (4) pMS (GAL4 DNA binding domain-vSrc kinase), and (5) pMS and pMAZ22.

The results of this assay are shown in FIG. 2. Cells transfected with carrier DNA do not release SEAP into the media (FIG. 2, col. 1). GAL4 DBD-vSrc kinase-Zeta ITAM fusion protein, when expressed in cells, is not a competent transcriptional activator (FIG. 2, col. 2). However, when in addition, VP16-tandem ZAP SH2 fusion protein is made in these cells, transcription is induced due to two-hybrid formation and the cells secrete copious amounts of SEAP into the culture media (FIG. 2, col. 3). Thus, the requirements necessary for the induction of SEAP production in HT1080 fibrosarcoma cells is consistent with the interaction of tyrosine phosphorylated Zeta ITAM and the tandem ZAP SH2 domains. The induction of SEAP production requires that both of the fusion proteins described above be expressed. The recognition and binding of tyrosine phosphorylated zITAM by the ZAP SH2 domains effectively bring the VP16 TAD to the promoter, thereby inducing transcription of the SEAP reporter gene.

Two hybrid formation is Zeta ITAM chain-dependent (compare FIG. 2, cols. 3 and 5). Furthermore, GAL4 DBD fusion proteins which lack the vSrc kinase domain (GAL4 DBD-Zeta ITAM), or which lack the Zeta chain, i.e., pMS (GAL4 DBD-vSrc kinase), fail to induce SEAP production when produced in cells alone or with pMAZ22, i.e., the VP16 TAD-tandem ZAP SH2 fusion protein (see FIG. 2, cols. 4 and 5). See, also, cols. 1, and 2 for controls. In addition to the results shown in FIG. 2, cells that contain plasmids that encode GAL4 DBD and VP16 TAD-tandem ZAP SH2, or GAL4 DBD-vSrc kinase-Zeta ITAM and VP16 TAD, fail to produce SEAP.

Hence, in a heterologous cell line the tandem ZAP-SH2:hITAM interaction that normally occurs in T-cells has been reproduced and a simple, sensitive means to monitor the extent to which these two molecules interact has been presented by this invention.

Using SEAP production as an indicator of the interaction of these two molecules, it is possible to identify compounds that can specifically inhibit ZAP SH2 domain-dependent interactions. When the host cells are cultured, they are exposed to test compounds. The extent to which the test compounds successfully interrupt the interaction between the ZAP SH2 and the zITAM indicates the presence of an SH2 inhibitor.

With the assay set up as described, one potential drawback when screening for molecules that inhibit ZAP SH2-dependent interactions is that the constitutive expression of the interacting components of the two-hybrid screen would result in constitutive ZAP SH2-Zeta ITAM complex formation. Hence, this embodiment of an assay identifies only compounds that efficiently disrupt two-hybrid formation.

Example 4

Transcriptionally Induced Two-Hybrid Formation: an Alternative Two-Hybrid Assay for Mammalian Cells Screen for Compounds that Inhibit Zap SH2 Domain Function In another embodiment of the assay of this invention, cells are exposed to potential inhibitory test compounds and then the interaction of proteins whose association is to be inhibited is induced. This embodiment of the assay depends on use of plasmids for the production of both the Zeta ITAM and tandem ZAP SH2 fusion proteins in the cells (as described in Example 2), which have inducible transcriptional regulatory sequences, rather than constitutive (i.e., SV40 virus based) transcriptional regulatory sequences.

An example of an inducible transcriptional regulatory sequence includes the mouse mammary tumor virus (MMTV) dexamethasone inducible promoter. Other known regulatory sequences are useful here. Thus, if, for example, the sequences encoding GAL4 DBD-vSrc kinase-Zeta ITAM fusion protein were linked to the MMTV inducible regulatory sequences, fusion protein production would be dexamethasone-dependent. The reporter cell line is then exposed to potential inhibitory compounds and two-hybrid formation is induced using dexamethasone. In this embodiment Zeta ITAM-tandem ZAP SH2 two-hybrid formation occurs if SH2 domain(s) binding is not affected by inhibitory compounds.

The mammalian G5-IL2 HT 1080 fibrosarcoma cell line (Example 2) is transfected with two effector plasmids by lipofection:

(1) One plasmid constitutively drives the expression of TAD—ZAP tandem SH2.

(2) The other plasmid encodes a fusion protein GAL4DBD-vSRC kinase domain—z ITAM expressed using the dexamethasone (Dex) inducible MMTV promoter.

These transfected mammalian cells are seeded in 96 well dishes and serial dilutions of test compounds are added to the wells. Dex is added to the media. Phosphorylated z ITAM fusion protein accumulates in cells upon the addition of Dex. After a 24 hour incubation, media is removed from the 96 well dish and placed into a second 96 well dish to perform a chromogenic or fluorescence assay for SEAP. The SEAP assay is measured using a 96 well plate reader. The amount of SEAP released into the media can be quantitated by using either a chromogenic or fluorescence assay.

By binding of the fusion protein to the ZAP SH2 domains, the TAD is brought to the SEAP promoter and SEAP is produced. Compounds will be present in cells to bind to ZAP SH2 domains before dex-induced production of phosphorylated h-ITAM occurs. Compounds that block ZAP SH2 function reduce SEAP production. Compounds that reduce SEAP production are analyzed using cells expressing SEAP in a ZAP SH2-independent manner to confirm that the compound is having a specific effect on ZAP:SH2-z ITAM complex formation.

Example 5

Two-Hybrid Assay Detects Beta ITAM-Src SH2 Domain-Dependent Two-Hybrid Formation in Mammalian Cells.

A two-hybrid assay useful for detecting Src tyrosine kinase SH2 domain-dependent interactions is performed as follows.

G5-IL2 HT 1080 cells (Example 2) were transfected with the following plasmid DNAs:
(a) pMSB (Example 1K: GAL4 DBD-vSrc kinase-BetaITAM);
(b) pMSB and pMAS2 (Example 1N: VP16-Src SH2); or
(c) pMSB and pMAZ22 (Example 1E: VP16-tandem ZAP SH2).

These transfected mammalian cells are seeded in 96 well dishes. Forty-eight hours after transfection, the amount of SEAP released into the media was determined using a fluorescence assay.

Figure 6:
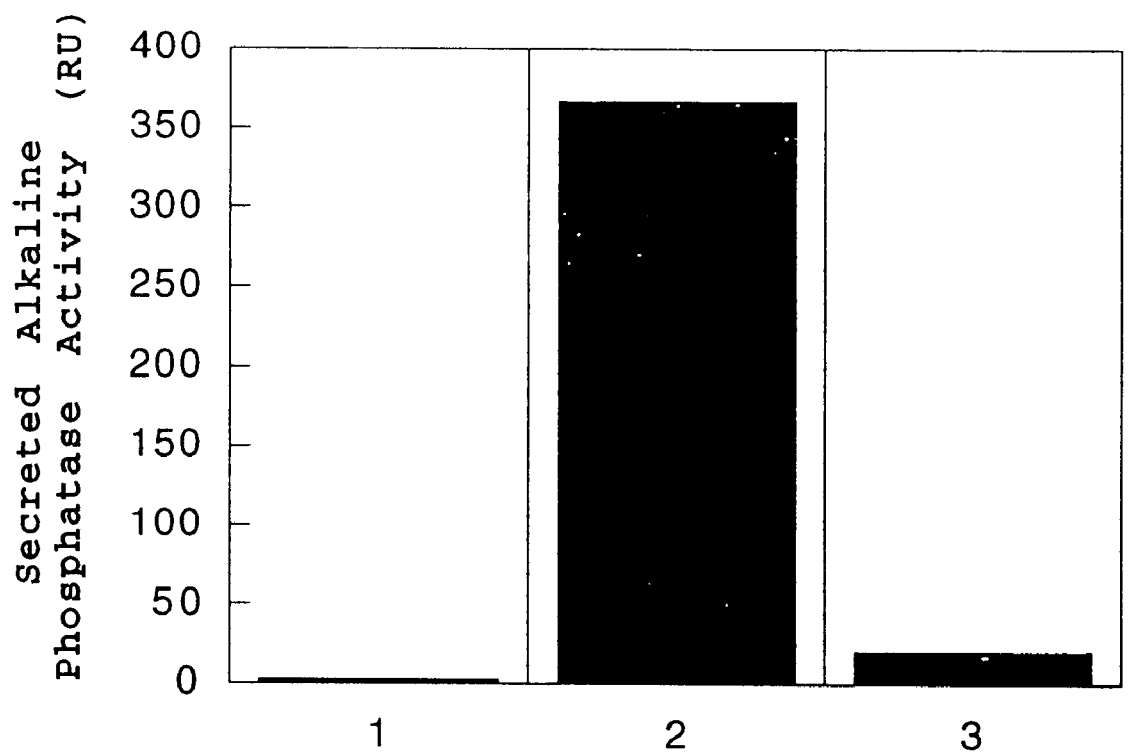
FIG. 6 is a bar graph plotting SEAP activity (RU) vs. specific Beta ITAM-Src SH2-dependent two-hybrid formation in mammalian cells transfected with piasmid DNAs, which correspond to the columns in the graph: (1) pMSB (Example 1K); (2) pMSB and pMAS2 (Example 1N); or (3) pMSB and pMAZ22.

The results are shown in FIG. 6, col. 1 illustrates that pMSB (GAL4 DBD-vSrc kinase-IgE receptor Beta ITAM fusion protein) is not by itself a competent transcriptional activator. However, when pMAS2 (VP16-Src SH2 fusion protein) is also present in cells, transcription is induced (see col. 2). In contrast, VP16-tandem ZAP SH2 does not efficiently interact with GAL4 DBD-vSrc kinase-Beta ITAM fusion protein to induce SEAP production (see col. 3).

When pMAS2 was co-expressed with GAL4 DBD-vSrc kinase-Zeta ITAM in the HT1080 fibrosarcoma indicator cell line, SEAP production was not observed (data not shown). If beta ITAM residues are replaced with the Zeta ITAM sequences, two-hybrid formation (SEAP production) is not observed using these conditions.9

Summarizing both Examples 4 and 5, two-hybrid formation appears to be ITAM and SH2 domain specific. The tandem ZAP SH2 domains bind to the Zeta ITAM (FIGS. 2 and 3), but not to the Beta ITAM (FIG. 6, col. 3). The Src SH2 domain efficiently binds to the Beta ITAM (FIG. 6) but not to Zeta ITAM residues. As observed when using the ZAP SH2 domains and Zeta ITAMs, Src SH2—dependent two-hybrid formation can be rendered inducible via the use of the estrogen receptor ligand binding domain residues, as discussed below.

Example 6

Post-Transcriptionally Induced Two-Hybrid Formation: a Steroid Dependent Two-Hybrid Assay for Mammalian Cells A. Estrogen Regulation of Zeta ITAM-tandem ZAP SH2 Dependent Two-Hybrid Formation in Mammalian Cells (transient transfections)

The mammalian G5-IL2 HT 1080 fibrosarcoma cell line (Example 2) is transtected with two effector plasmids by iipofection:

1) pMerSZ (Example 1F) drives the production of GAL4 DBD-ER l.b.d.-vSrc kinase-Zeta ITAM fusion protein in mammalian cells.

2) pMAZ22, VP16 TAD-tandem ZAP SH2 (Example 1E).

For controls and comparisons. the G5IL-2 HT1080 cells were also transfected with carrier DNA, or with pMSZ only, or with pMSZ and pMAZ22, or with pMerSZ only.

Each of these transfected mammalian cells are seeded in 6 well dishes and serial dilutions of test compounds are added to the wells. Twenty-four hours after transfection, one duplicate dish of cells was cultured in the presence of 10 nM estrogen.

Forty-eight hours after transfection, an aliquot of media from all of the dishes was removed from the 6 well dish and placed into a 96 well dish to perform a chromogenic or fluorescence assay for SEAP activity.

Figure 3:
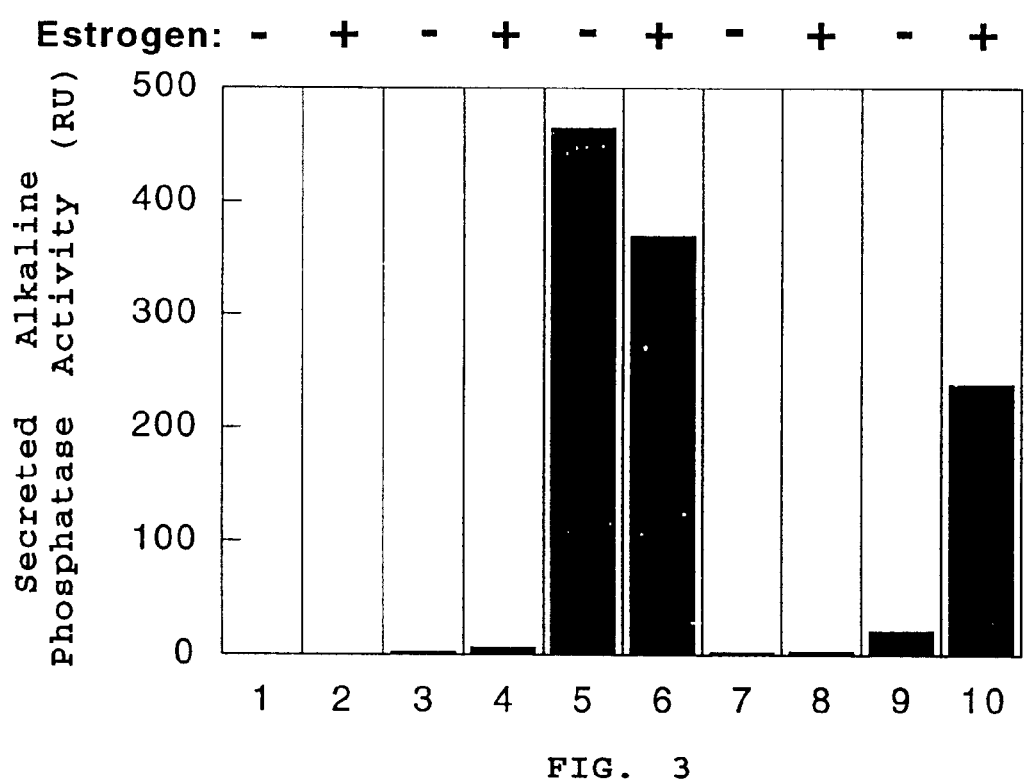
FIG. 3 illustrates an estrogen-regulated assay system. The bar graph depicts the results observed in the presence (+) and absence (−) of estrogen on Zeta ITAM-tandem ZAP SH2 dependent two-hybrid formation in mammalian G5IL-2 HT1080 cells. SEAP activity is plotted against cells which received plasmid DNAs in duplicate, i.e., cols. 1 and 2 are carrier DNA; cots. 3 and 4 are PMSZ; cots. 5 and 6 are pMSZ and pMAZ2; cols. 7 and 8 are pMerSZ (Example 1 F); and cols. 9 and 10 are pMerSZ and pMAZ22.

FIG. 3 provides the results of this assay: The cell line transfected with carrier DNA is reported in cols. 1 and 2; or with pMSZ (Example 1D) in cols. 3 and 4; or with both pMSZ and pMAZ22 in cols. 5 and 6. Cols. 7 and 8 are the results of the cell line transfected only with plasmid pMerSZ. Cols. 9 and 10 are results of the cell line transfected with both pMerSZ and pMAZ22, as described above.

The addition of the estrogen receptor l.b.d. residues to the GAL4 DBD-vSrc kinase-Zeta ITAM fusion protein makes two-hybrid formation estrogen-dependent (compare FIG. 3, cols. 9–10). That is, in the absence of exogenously added estrogen, the fusion protein (GAL4-DBD-ER l.b.d.-vSrc kinase-g-ITAM) is not functional. In fact, FIG. 3, col. 9 shows that only low levels of SEAP are detected in the media. This is presumably due to the low levels of estrogen present in serum. Low levels of SEAP are not observed if the cells are cultured in a defined synthetic media lacking estrogen. When plasmids pMerSZ and pMAZ22 are expressed together in cells, two-hybrid formation (reporter gene transcription) should not occur (col. 9), unless estrogen is present in the media (col. 10). When these transfected cells were exposed to 10 nM estrogen, copious amounts of SEAP was released into the media.

Estrogen did not markedly affect two-hybrid formation it the estrogen receptor l.b.d. was not present in either plasmid expressing fusion protein (cols. 5 and 6). Also, the estrogen receptor l.b.d. residues do not make the GAL4 DBD-vSrc kinase-Zeta ITAM fusion protein itself a transcriptional activator (FIG. 3, Cols. 7 and 8).

Figure 5:
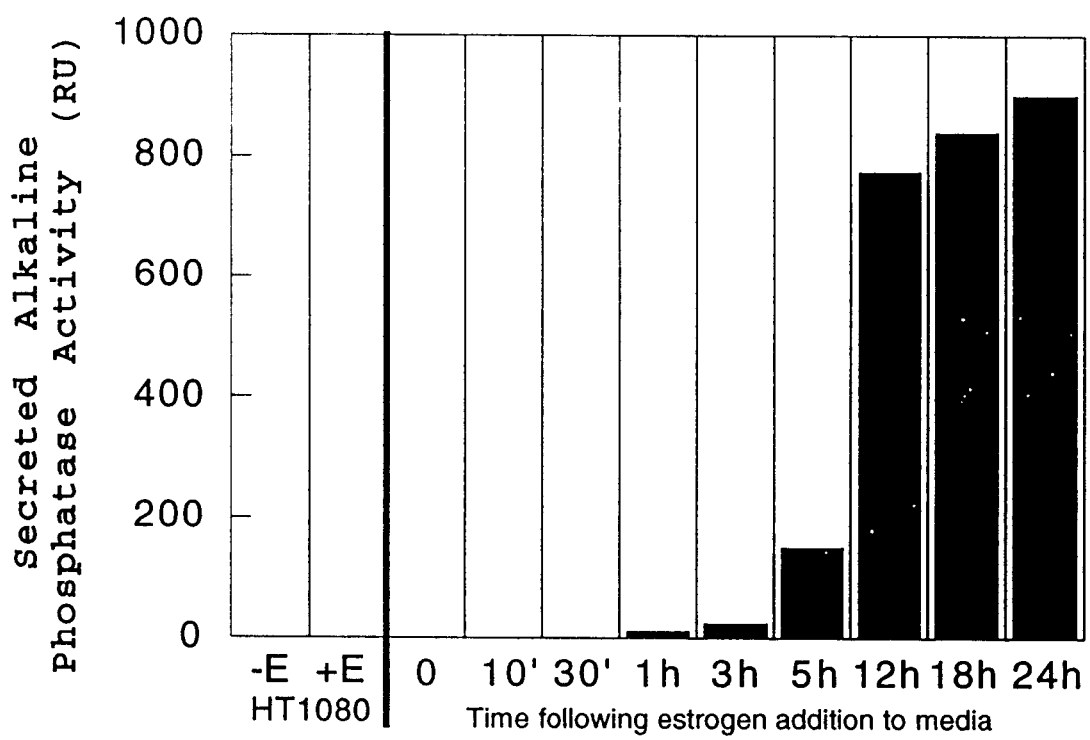
FIG. 5 is a bar graph plotting the time course of SEAP production (RU) in Clone D with inducible Zeta ITAM-tandem ZAP SH2-dependent two-hybrid activity vs. time following estrogen addition to media from 0 minutes to 24 hours. The graph also illustrates that parent cells (unengineered G51L-2 HT1080 cells) do not produce SEAP when cultured in the presence (+E) or absence (−) of estrogen.

SEAP induction was time-dependent, the majority of the SEAP was produced 12–18 hours after exposure of the cells to estrogen (see FIG. 5 for analogous results with stably transfected cells).

B. Estrogen Regulation of Beta ITAM-src SH2-Dependent Two-Hybrid Formation in Mammalian Cells (transient transtection).

In a manner similar to that described above for the Zeta ITAM constructs, G5-IL2 HT 1080 cells were transfected with the following plasmid DNA (in duplicate): pMerSB or pMerSB and pMAS2. Twenty-four hours after transfection, one dish of cells was cultured in the presence of 10 nM estrogen. Another twenty-four hours later, an aliquot of media from all of the dishes was analyzed for SEAP activity.

Figure 7:
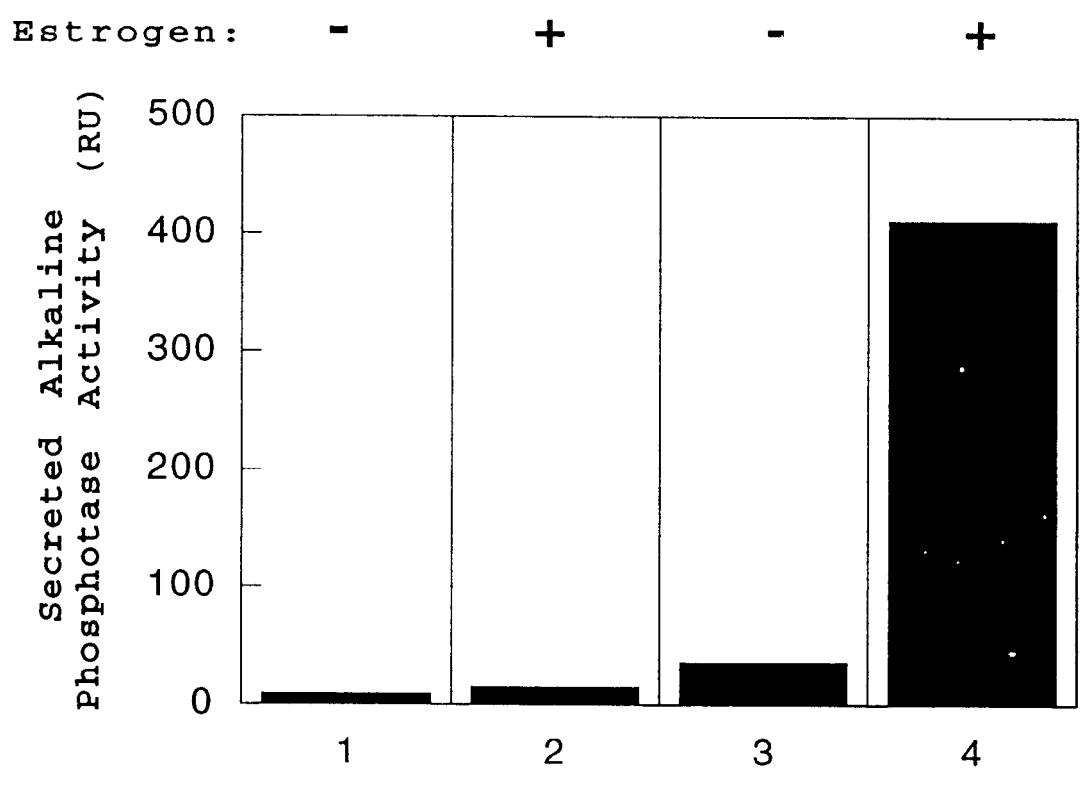
FIG. 7 is a bar graph plotting SEAP activity (RU) vs. estrogen regulation of Beta ITAM-Src SH2-dependent two-hybrid formation in mammalian cells. The presence (+) or absence (−) of estrogen is indicated. The columns represent cells transfected in duplicate with pMerSB (Example 1L) [Cols. 1 and 2] or with pMerSB and pMAS2 (Example 1N) [Cols. 3 and 4].

As shown in FIG. 7, the presence (+) or absence (−) of estrogen is indicated, and the columns represent cells transfected with pMerSB (Example 1L) [Cols. 1 and 2] or with pMerSB and pMAS2 (Example 1N) [Cols. 3 and 4]. The addition of the estrogen receptor l.b.d. residues to the GAL4 DBD-vSrc kinase-Beta ITAM fusion protein makes two-hybrid formation estrogen-dependent (compare cols. 3 and 4). In contrast, the estrogen receptor l.b.d. residues do not make the GAL4 DBD-vSrc kinase-Beta ITAM fusion protein itself a transcriptional activator (cols. 1 and 2).

C. Stable Cell Line that Constitutively Expresses GAL4 DBD-Estrogen Receptor l.b.d.-Src Kinase-g-ITAM and ZAP-SH2 Activation Domains in Mammalian Cells.

G5IL-2 HT1080 cells that contain an integrated GAL4-dependent SEAP reporter gene (Example 2) were transfected with pBabeNeo (neomycin selection), pMerVP (Example 10), and the two effector plasmids that drive the constitutive production of GAL4 DBD-estrogen receptor l.b.d.-vSrc kinase-Zeta ITAM and VP 16 TAD-tandem ZAP SH2, i.e., pMerSZ (Example 1F) and pMAZ22 (Example 1E), respectively, were transfected into the cells with neomycin.

After selection with both hygromycin and neomycin, cell lines were generated that contain the reporter gene (hygromycin selection) and both effector plasmids (neomycin selection). Individual colonies were isolated and expanded. One set of duplicate cells was exposed to 10 nM estrogen. Both duplicate sets of cells were assayed for estrogen-induced (+inducer) SEAP activity. Those with markedly induced SEAP production were expanded for further analysis.

Figure 4:
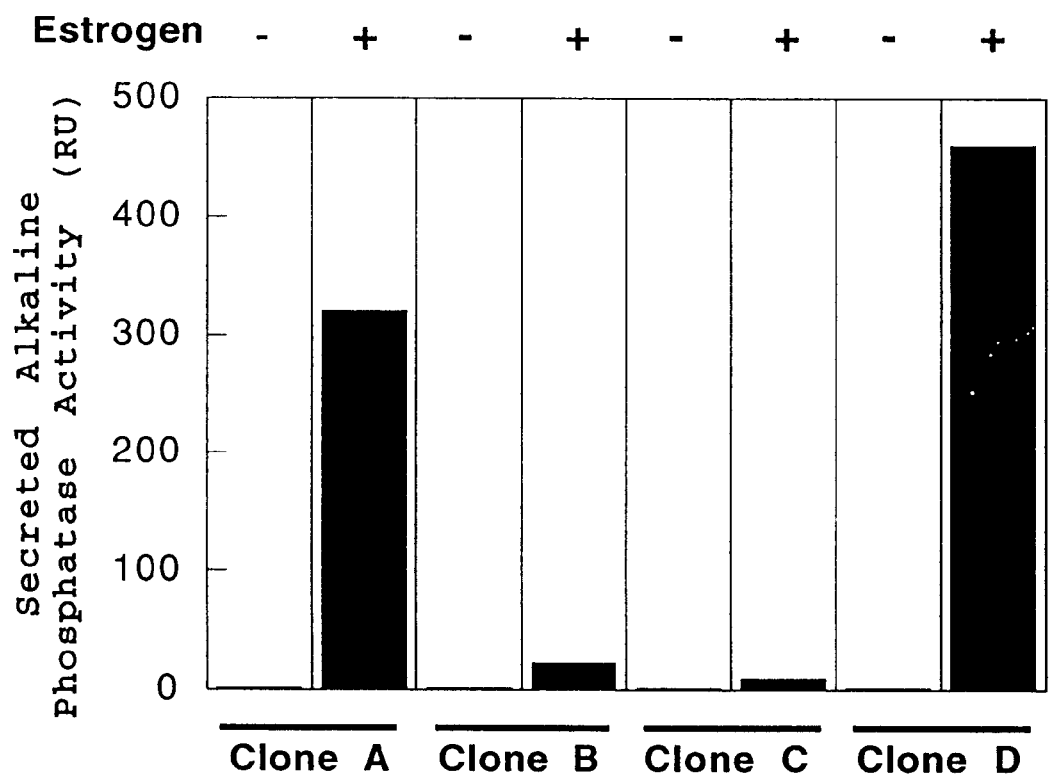
FIG. 4 is a bar graph of a ZAP two-hybrid assay plotting SEAP activity units vs. four stable clones A through D, each grown with (dark bar) or without (light bar) inducer (estrogen).

Of the twelve colonies containing MerSZ and MAZ22 that were analyzed, five exhibited high levels of SEAP activity after exposure to estrogen (FIG. 4). Two of these clones (clone A and clone D) exhibited very high levels of estrogen-induced SEAP gene expression. The amount of SEAP in the media induced 200-told (cell line #3) and 600-fold (cell line #6) after the addition of 10 nM estrogen. Stable cell lines that combined estrogen-regulated MerUP were also obtained (Example 6D).

The time course of SEAP production this stable cell line with inducible Zeta ITAM-tandem ZAP SH2-dependent two-hybrid activity was studied as followed. Clone D (FIG. 4) was cultured in the presence of 10 nM estrogen and, at various times after the addition of estrogen, culture media was assayed for the presence of SEAP activity. As shown in FIG. 5, the bulk of SEAP production occurs by 12 hours. Clone D cells do not produce appreciable amounts of SEAP when estrogen is exogenously added to the media (see FIG. 4). Also, the parent cells (G5IL-2 HT1080 cells) do not produce SEAP when cultured in the presence of 10 nM estrogen for 24 hours (compare −E, +E columns of FIG. 5).

D. Control Cell Line

When screening for compounds that block SH2-dependent two-hybrid formation (SEAP production), compounds that have nonspecific effects will also be identified. Such compounds include those that are cytotoxic, those that affect transcription, translation or secretion, those that affect GAL4 DNA binding or the estrogen receptor ligand binding domain. Hence, compounds that are identified using the SH2 dependent assay are tested using a cell line that constitutively expresses GAL4 DBD-estrogen receptor l.b.d.-VP16 fusion protein.

Figure 8:
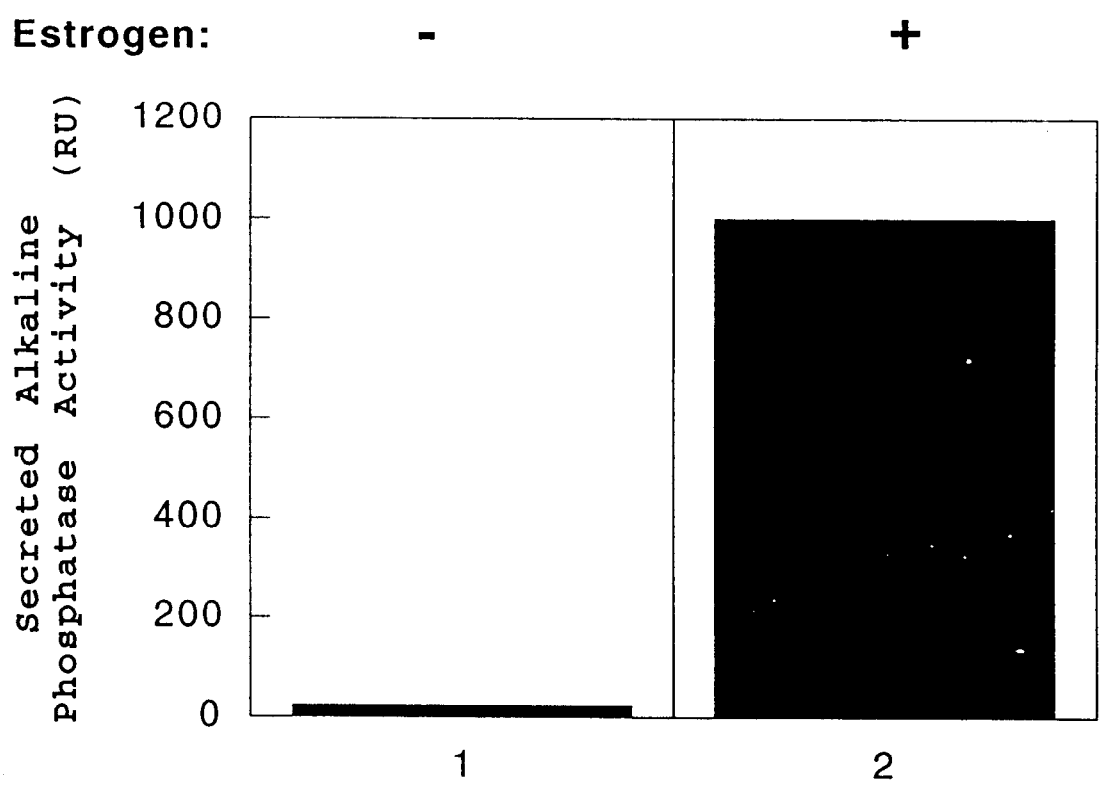
FIG. 8 is a bar graph plotting SEAP activity (RU) of a stable mammalian cell line containing an inducible GAL4-estrogen receptor l.b.d.-VP16 transcription activator in the presence (+) or absence (−) of estrogen.
Figure 9:
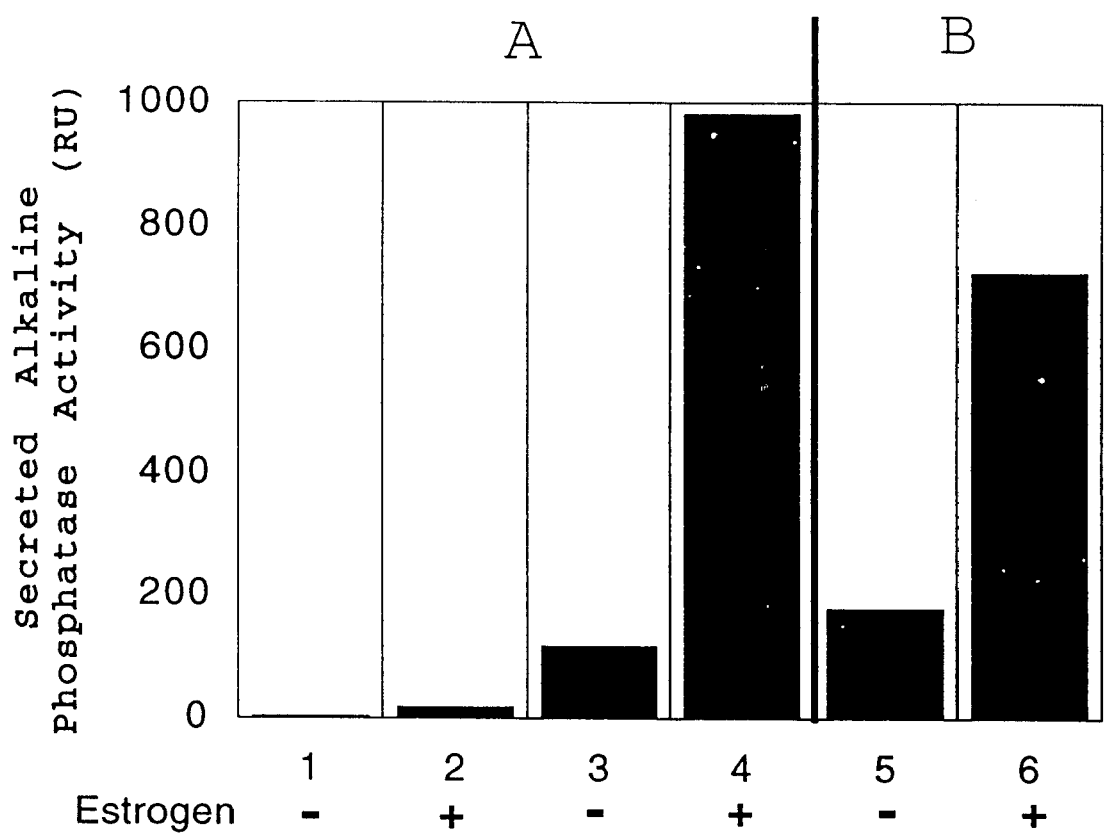
FIG. 9 is a bar graph plotting SEAP activity (RU) vs. estrogen regulation of Beta ITAM-Fyn SH2-dependent two-hybrid formation in mammalian cells observed by transient transfection (FIG. 9, panel A, columns 1–4 of the graph) or when using a stable cell line (FIG. 9, panel B, column 5 and 6). The presence (+) or absence (−) of estrogen is indicated. The columns represent cells transfected in duplicate with pMerSB (Example 1L) [Cols. 1 and 2] or with pMerSB and pMAF2 (Example 1P) [Cols. 3 and 4]. Columns 5 and 6 represent a stable cell line (prepared as described in example 2) containing both pMerSB and pMAF2 cultured in the absence (column 5) or presence (column 6) of estrogen.

The results with one clone (cell line 6), containing an inducible GAL4-estrogen receptor l.b.d.-VP16 transcriptional activator in the presence (+) or absence (−) of estrogen, are shown in FIG. 8. Compounds that exert non-specific effects as described above will score positive when using this cell line.

Example 7

Methods for Characterizing Binding Activity of an Inhibitor Identified by the Method of this Invention Several methods for characterizing binding activity (e.g., counter-screens) of an inhibitor identified by the present invention are discussed below, where the PBD is an SH2 domain of interest.

1. Competitive Binding Assays:

Binding is measured by competition using surface plasmon resonance [Malmqvist, M., *Curr Opin. Immunol.*, 5, 282–286 (1993)] as implemented in the BIAcore® Biosensor (Pharmacia Biosensor, Piscataway, N.J.). SH2 proteins, e.g. pp60src, pp70ZAP, or pp72syk, are pre-incubated with various concentrations of test compound and the ability of the test compound to competitively inhibit binding to a phophopeptide ligand measured. Results are compared to binding measured in the absence of competitor and expressed as percent inhibition.

IC50 values reflect the concentration of inhibitor required to reduce binding by 50%. Specifics of individual assays are described below. All assays are run in HEPES Buffered Saline (HBS) composed of 10 mM HEPES (pH 7.4)/150 mM NaCl/3.4 mM EDTA/0.05% Surfactant P20 at 25° C. and a flow rate of 5 uL min-1.

a. Specifics of Tandem Syk Assay

A pp72syk peptide ligand corresponding to the g-chain ITAM of human FceRI [DGVY(PO4)TGLSTRNQETY(PO4)ETLK [SEQ ID NO:17]] was synthesized as part of a larger peptide [Ac-CGGDGVY(PO4)TGLSTRNQETY-(PO4)ETLK-NH2 [SEQ ID NO:18]] and used to generate a Syk-sensitive biosensor surface. Specifically, a Biosensor Chip CM5 was activated with 200 mM ethyl-3-(3-dimethylaminopropyl)-carbodiimide hydrochloride (EDC)/50 mM n-hydroxysuccinimide (NHS) to generate a surface reactive to primary amines; treated with ethylenediamine to generate a surface rich in primary amines; activated with m-maleimidobenzoyl-n-hydroxysuccinimide ester (sulfo-MBS; 50 mM in 25 mM NaHCO3) to generate a surface reactive to free thiois; and the ITAM peptide immobilized through the n-terminal cysteine. Unreacted sites were blocked with b-mercaptoethanol and the chip cleaned of noncovalently bound peptide using 6 M guanidine hydrochloride. Assays were run in HBS using 20 nM pp72syk (1–265) +/− test inhibitor.

b. Specifics of C-Syk Assay

A pp72syk peptide ligand corresponding to a hemiphosphorylated g-chain ITAM of human fceRI [DGVY(P04)TGLSTRNQETYETLK [SEQ ID NO:19]] was synthesized as part of a larger peptide [Ac-CGGDGVY(P04)TGLSTRNOETYETLK-NH2 [SEQ ID NO:20]] and used to generate a C-Syk-sensitive biosensor surface as described above for tandem syk. Assays were run in HBS using 270 nM pp72syk(163–265) +/− test inhibitor.

c. Specifics of Tandem ZAP Assay

A pp7OZAP peptide ligand corresponding to the z-chain ITAM-1 of the human T-cell receptor [NOLY(P04)NELNIGRREEY(PO4)DVLD [SEQ ID NO:21]] was synthesized as a part of a larger peptide [Ac-KGGNQLY(P04)NELNIGRREEY-(PO4)DVLD-NH2 [SEQ ID NO:22] and used to generate a ZAP-sensitive biosensor surface. Specifically, a Biosensor Chip CM5 was activated with 200 mM EDC/50 mM NHS to generate a surface reactive to primary amines and the ITAM peptide immobilized through the n-terminal lysine. Unreacted sites were blocked with ethanolamine (1 M in water) and the chip cleaned of noncovalently bound peptide using 6 M guanidine hydrochloride. Assays were run in HBS using 10 nM pp70(1–259) +/− test inhibitor.

d. Specifics of Src Assay

A p60src peptide. ligand corresponding to the hamster MiddleT antigen [QY(PO4)EEIPI [SEQ ID NO:231]] was synthesized as a part of a larger peptide [Ac-KGGQY(P04)EEIPI-NH2 [SEQ ID NO:24]] and used to generate a src-sensitive biosensor surface as described above for tandem ZAP. Assays were run in HBS using 270 nM pp60src (144–251) +/− test inhibitor.

Example 8

Yeast-Based Two-Hybrid Screening Assays

The constitutive as well as inducible Src SH2- and ZAP SH2 dependent two-hybrid systems described here using mammalian cells are also useful with yeast cells. A yeast strain which contains an integrated reporter gene consisting of the β-galactosidase gene linked to a promoter that is GAL4-dependent has been demonstrated. Two-hybrid formation induces β-galactosidase production, which can be detected using an enzyme assay, or from the blue color produced when cells producing enzyme are exposed to X-GAL. As with mammalian cells, SH2-dependent two-hybrid formation in yeast can be rendered estrogen-dependent using the estrogen receptor ligand binding domain.

A yeast strain such as the one that contains a mutation in the srb1 gene is used for the two-hybrid assay. Cells containing the tsl allele of srb1 exhibit increased endocytosis and have generally increased permeability. Cells are engineered so that plasmids used for the two-hybrid screen can be selectively propagated.

a) HIS3–1,2,4 triazole Assay

In this assay, cells auxotrophic for histidine are transformed with a HIS3 gene controlled by a promoter that contains LexA DNA binding sites. The tandem SH2 domains of ZAP are expressed in cells linked to the LexA DBD. This fusion protein binds to DNA, but is not a competent transcriptional activator. The TCR z ITAM sequence is also expressed in the cells, as part of a hybrid protein that includes a nuclear localization sequence, the Lck tyrosine kinase catalytic domain and a transcriptional activation domain. The Lck kinase domain should be active and in the nucleus, with the potential to phosphorylate the tyrosine residues of z ITAM sequence either in cis or in trans.

The interaction of the phosphorylated z ITAM-transcriptional activation domain fusion protein with the ZAP SH2 domains-LexA protein activates HIS3 transcription, generating cells that can grow in media lacking histidine. Compounds that interfere with the interaction of the ZAP SH2 domains with phosphorylated z ITAM will reduce the level of HIS3 transcription. Compounds that efficiently block this interaction prevent yeast growth in media lacking histidine. However, compounds that weakly disrupt ZAP SH2-z ITAM association are not detected as histidine production by the cell must be dramatically reduced to affect viability.

The sensitivity of this assay can be adapted to be able to detect molecules that weakly block ZAP SH2-z ]TAM association. Cells are grown in the presence of 3-amino-1, 2,4-triazole, a competitive inhibitor of histidine. Cells are cultured using a concentration of 3-amino-1,2,4-triazole that is just below the amount required to affect cell viability. Compounds that trigger even a small reduction of HIS3 transcription are identified as the affected cells will no longer grow.

There are two counterscreens useful to evaluate whether compounds that score in the above assay exert their effect on growth by specifically affecting ZAP SH2-z ITAM association. In one counterscreen, the cells are cultured in the presence of histidine. ZAP SH2 inhibitors do not affect the growth of cells under this condition. In a second counterscreen, an identical yeast strain is established except that the transcription of HIS3 is driven by a monomer of the LexA DBD genetically fused to the activation domain, thus the transcription of the HIS3 gene is not dependent on ZAP SH2-z ITAM association.

Specifically, the yeast host cells in log phase growth are seeded in 96 well dishes (0.1 mis of cells) in media that lacks histidine and contains 3-amino-1,2,4-triazole. Serial dilutions of compound are added to wells. The cultures are incubated 1–2 days at 300C on a shaker platform. The affect of compounds on growth is assessed using a 96 well plate reader.

This assay depends on growth inhibition (the interference of two-hybrid dependent HIS3 transcription) as the readout. Secondary assays should be performed to confirm that the compounds that scored positive are not toxic to yeast.

b ) URA3/5-FOA Assay:

The second approach for identifying molecules that inhibit ZAP SH2 binding in yeast scores inhibitory compounds based on the ability to block ZAP two-hybrid dependent cell death. In this assay, the tandem ZAP SH2 domain is expressed in yeast fused to the LexA DBD and the z ITAM-Lck domain is fused to transcriptional activation as in the constructions described above. However in this assay, the reporter gene, which is regulated by the LexA DBD is the URA3 gene.

Cells which express the URA3 gene product die when exposed to 5-fluoro-orotic acid (5-FOA). The product of the URA3 gene converts 5-FOA to fluorodeoxyuridine, which is a potent inhibitor of thymidylate synthetase. Hence 5-FOA is conditionally toxic to cells. Compounds that interfere with tandem ZAP SH2-z ITAM complex formation reduce the amount of URA3 gene product. By carefully titrating the amount of "two-hybrid" transcriptional activator in the cell and by using the lowest concentration of 5-FOA that will still kill cells, conditions are defined where compounds that disrupt the ZAP SH2-z ITAM interaction are identified. Such molecules reduce the URA3 gene product levels (and hence the fluorodeoxyuridine levels) below the level where toxic amounts of iluorodeoxuridine levels are formed.

In contrast to the assay of 8A above, toxic compounds are not scored when using the "URA3/5-FOA" screen, which is a cell viability assay.

Example 9

Association of Src Protein with Tyrosine Phosphorylated Proteins in Vivo

Several proteins have been reported to coprecipitate with v-Src from extracts of v-Src-transformed cells [Kanner, S. B. et al., *EMBO J.*, 10:1689–1698 (1991); Koch, C. A., *Mol. Cell. Biol.*, 12:1366–1374 (1992)]. The ability of a high affinity Src SH2-binding peptide [EPQpYEEIPI, denoted here as YEEI [SEQ ID NO:25]] to block SH2 domain-dependent interactions is demonstrated in this assay.

In this assay, Balb/c 3T3 and SRD-3T3 cells (V-Src transformed 3T3 cells) were lysed in RIPA buffer and the Src protein was immunoprecipitated with a monoclonal antibody to the amino-terminus of Src in the presence or absence of the SH2 and SH3 binding peptides. The samples were transferred to nitrocellulose, and the blot was probed with a monoclonal antibody to phosphotyrosine. Two major tyrosine phosphorylated proteins co-migrated with v-Src from SRD 3T3 cells, one of which co-migrated with the 62 kDa tyrosine-phosphorylated protein that bound to the Src SH3 domain, and the other protein of Mr 130,000, which is most likely the 130,000 kDa protein previously detected in v-Src immunoprecipitates [Koch, C. A., *Mol. Cell. Biol.*, 12:1366–1374 (1992)].

The binding of Src to the 62 kDa protein was reduced significantly by incubation of the extracts with the "Src-pro" peptide or the phosphorylated YEEI [SEQ ID NO:25] peptide, but not the poly-proline nor the unphosphorylated YEEI [SEQ ID NO:25] peptides, suggesting that both the SH2 and SH3 domains of Src are required for stable association of this protein with Src. This protein has not been determined to be the p62 protein identified in the total cell SH3 binding proteins since the p62 antibody is not sensitive enough to recognize the small amounts of the 62 kDa protein that associate with Src under these conditions. The "Src-pro" peptide and the pYEEI [SEQ ID NO:25] peptide could only block 50% of p130 binding to Src, whereas 90% inhibition of p130 binding was observed when both peptides were used, suggesting that either the SH2 or the SH3 domain is sufficient for some degree of p130 association with Src.

This invention is not to be limited in scope by the specific embodiments described herein. Indeed, various modifications of the invention in addition to those described herein will become apparent to those skilled in the art from the foregoing description. Such modifications are intended to fall within the scope of the appended claims.

The disclosures of the patents, patent applications and publications cited herein are incorporated by reference in their entireties.

What is claimed is:

1. A method for identifying the presence in a test composition of an inhibitor of the binding of a phosphopeptide binding pair comprising either a phosphatase domain and a ligand therefor or a phosphotyrosine binding domain and a ligand therefor, which method comprises the steps of:
   (a) providing mammalian cells which contain and are capable of expressing recombinant DNA molecules encoding two fusion proteins, the first of which comprising one or more copies of each of a transcription activation domain and one member of the phosphopeptide binding pair, the second of which comprising one or more copies of each of a DNA-binding domain and the other member of the phosphopeptide binding pair, wherein the cells
      (i) further contain a reporter gene which encodes a detectable gene product and is linked to a DNA sequence permitting expression of the reporter gene in the presence of the pair of fusion proteins, and
      ii) when cultured are capable of producing measurable amounts of said detectable gene product,
   (b) culturing said cells in the presence and absence of the test composition under conditions in which, in the absence of an inhibitor of the binding of the phosphopeptide binding pair they produce measurable amounts of said detectable gene product, and
   (c) determining whether production of the detectable gene product was diminished in the presence of the test composition which would indicate the presence of an inhibitor.

2. The method according to claim 1 wherein said cell is a mammalian cell.

3. The method according to claim 1, wherein the DNA-binding domain and transcriptional activation domain are derived from transcriptional activators having separable DNA-binding and transcriptional activation domains.

4. The method according to claim 3, wherein the DNA binding domain and the transcriptional activation domain are selected from he group consisting of transcriptional activators GAL4, GCN4 and ADR1.

5. The method according to claim 1, wherein the DNA-binding domain and the transcriptional activation domain are from different transcriptiqnal activators.

6. The method according to claim 1 wherein said phosphopeptide binding pair comprises an SH2 domain and a ligand therefor, a phosphatase domain and a ligand therefor, or a PID phosphopeptide binding domain and a ligand therefor.

7. The method according to claim 1 wherein the first fusion protein contains two phosphopeptide binding domains.

8. The method according to claim 1 wherein one of the fusion proteins further contains a hormone binding domain permitting regulated sequestering of the fusion protein.

9. The method according to claim 1 wherein said test composition is selected from a mixture of one or more test peptides, wherein said mixture is provided in the form of a library of synthetic peptides or in the form of a phage library displaying the various peptides.

10. The method according to claim 1 wherein said ligand is an immunoreceptor tyrosine activation motif (ITAM).

11. The method according to claim 10 wherein said ITAM is the TCR zeta ITAM.

* * * * *

SEQUENCE LISTING

<160> NUMBER OF SEQ ID NOS: 25

<210> SEQ ID NO 1
<211> LENGTH: 25
<212> TYPE: DNA
<213> ORGANISM: Rous sarcoma virus

<400> SEQUENCE: 1
cggaattctc caagccccag accca                                   25

<210> SEQ ID NO 2
<211> LENGTH: 25
<212> TYPE: DNA
<213> ORGANISM: Rous sarcoma virus

<400> SEQUENCE: 2
gcggatccct cagcgacctc caaca                                   25

<210> SEQ ID NO 3
<211> LENGTH: 29
<212> TYPE: DNA
<213> ORGANISM: Homo sapiens

<400> SEQUENCE: 3
cggaattctc tgctggagac atgagagct                               29

<210> SEQ ID NO 4
<211> LENGTH: 28
<212> TYPE: DNA
<213> ORGANISM: Homo sapiens

<400> SEQUENCE: 4
cggaattcga ctgtggcagg gaaaccct                                28

<210> SEQ ID NO 5
<211> LENGTH: 27
<212> TYPE: DNA
<213> ORGANISM: Homo sapiens

<400> SEQUENCE: 5
gcggatccgg agctggggaa gaactca                                 27

<210> SEQ ID NO 6
<211> LENGTH: 30
<212> TYPE: DNA
<213> ORGANISM: Homo sapiens

<400> SEQUENCE: 6
acgcgtcgac ttataaatca atgggaggag                              30

<210> SEQ ID NO 7
<211> LENGTH: 36
<212> TYPE: DNA
<213> ORGANISM: Homo sapiens

<400> SEQUENCE: 7
cctcacgaat tcggtggagt gaccaccttt gtggcc                       36

<210> SEQ ID NO 8
<211> LENGTH: 35
<212> TYPE: DNA
<213> ORGANISM: Homo sapiens

<400> SEQUENCE: 8
ccactcggat ccgccggggc acacggtggt gaggc                                35

<210> SEQ ID NO 9
<211> LENGTH: 36
<212> TYPE: DNA
<213> ORGANISM: Homo sapiens

<400> SEQUENCE: 9
cctcacgaat tcggcgactc catccaggct gaggag                               36

<210> SEQ ID NO 10
<211> LENGTH: 35
<212> TYPE: DNA
<213> ORGANISM: Homo sapiens

<400> SEQUENCE: 10
ccactcggat ccgccggggc acacggtggt gaggc                                35

<210> SEQ ID NO 11
<211> LENGTH: 36
<212> TYPE: DNA
<213> ORGANISM: Homo sapiens

<400> SEQUENCE: 11
cctcacgaat tcggtggagt gaccaccttt gtggcc                               36

<210> SEQ ID NO 12
<211> LENGTH: 35
<212> TYPE: DNA
<213> ORGANISM: Homo sapiens

<400> SEQUENCE: 12
ccactcggat ccgccggggc acacggtggt gaggc                                35

<210> SEQ ID NO 13
<211> LENGTH: 36
<212> TYPE: DNA
<213> ORGANISM: Homo sapiens

<400> SEQUENCE: 13
cctcacgaat tcggcgactc catccaggct gaggag                               36

<210> SEQ ID NO 14
<211> LENGTH: 35
<212> TYPE: DNA
<213> ORGANISM: Homo sapiens

<400> SEQUENCE: 14
ccactcggat ccgccggggc acacggtggt gaggc                                35

<210> SEQ ID NO 15
<211> LENGTH: 26
<212> TYPE: DNA
<213> ORGANISM: herpes simplex virus 7

<400> SEQUENCE: 15
cgggatccag cctgggggac gagctc                                          26

<210> SEQ ID NO 16
<211> LENGTH: 26
<212> TYPE: DNA

```
<213> ORGANISM: herpes simplex virus 7

<400> SEQUENCE: 16
ggactagtcc caccgtactc gtcaat                                        26

<210> SEQ ID NO 17
<211> LENGTH: 19
<212> TYPE: PRT
<213> ORGANISM: Homo sapiens
<220> FEATURE:
<221> NAME/KEY: MOD_RES
<222> LOCATION: (4)
<223> OTHER INFORMATION: PHOSPHORYLATION
<220> FEATURE:
<221> NAME/KEY: MOD_RES
<222> LOCATION: (15)
<223> OTHER INFORMATION: PHOSPHORYLATION

<400> SEQUENCE: 17

Ala Gly Val Tyr Thr Gly Leu Ser Thr Arg Asn Gln Glu Thr Tyr Glu
  1               5                  10                  15

Thr Leu Lys

<210> SEQ ID NO 18
<211> LENGTH: 22
<212> TYPE: PRT
<213> ORGANISM: Homo sapiens
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (7)
<223> OTHER INFORMATION: PHOSPHORYLATION
<220> FEATURE:
<221> NAME/KEY: MOD_RES
<222> LOCATION: (18)
<223> OTHER INFORMATION: PHOSPHORYLATION
<220> FEATURE:
<221> NAME/KEY: MOD_RES
<222> LOCATION: (22)
<223> OTHER INFORMATION: AMIDATION

<400> SEQUENCE: 18

Cys Gly Gly Asp Gly Val Tyr Thr Gly Leu Ser Thr Arg Asn Gln Glu
  1               5                  10                  15

Thr Tyr Glu Thr Leu Lys
              20

<210> SEQ ID NO 19
<211> LENGTH: 19
<212> TYPE: PRT
<213> ORGANISM: Homo sapiens
<220> FEATURE:
<221> NAME/KEY: MOD_RES
<222> LOCATION: (4)
<223> OTHER INFORMATION: PHOSPHORYLATION

<400> SEQUENCE: 19

Asp Gly Val Tyr Thr Gly Leu Ser Thr Arg Asn Gln Glu Thr Tyr Glu
  1               5                  10                  15

Thr Leu Lys

<210> SEQ ID NO 20
<211> LENGTH: 22
<212> TYPE: PRT
<213> ORGANISM: Homo sapiens
```

-continued

```
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (7)
<223> OTHER INFORMATION: PHOSPHORYLATION
<220> FEATURE:
<221> NAME/KEY: MOD_RES
<222> LOCATION: (22)
<223> OTHER INFORMATION: AMIDATION

<400> SEQUENCE: 20

Cys Gly Gly Asp Gly Val Tyr Thr Gly Leu Ser Thr Arg Asn Gln Glu
 1               5                  10                  15

Thr Tyr Glu Thr Leu Lys
            20

<210> SEQ ID NO 21
<211> LENGTH: 19
<212> TYPE: PRT
<213> ORGANISM: Homo sapiens
<220> FEATURE:
<221> NAME/KEY: MOD_RES
<222> LOCATION: (4)
<223> OTHER INFORMATION: PHOSPHORYLATION
<220> FEATURE:
<221> NAME/KEY: MOD_RES
<222> LOCATION: (15)
<223> OTHER INFORMATION: PHOSPHORYLATION

<400> SEQUENCE: 21

Asn Gln Leu Thr Asn Glu Leu Asn Ile Gly Arg Arg Glu Glu Tyr Asp
 1               5                  10                  15

Val Leu Asp

<210> SEQ ID NO 22
<211> LENGTH: 22
<212> TYPE: PRT
<213> ORGANISM: Homo sapiens
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (7)
<223> OTHER INFORMATION: PHOSPHORYLATION
<220> FEATURE:
<221> NAME/KEY: MOD_RES
<222> LOCATION: (18)
<223> OTHER INFORMATION: PHOSPHORYLATION
<220> FEATURE:
<221> NAME/KEY: MOD_RES
<222> LOCATION: (22)
<223> OTHER INFORMATION: AMIDATION

<400> SEQUENCE: 22

Lys Gly Gly Asn Gln Leu Thr Asn Glu Leu Asn Ile Gly Arg Arg Glu
 1               5                  10                  15

Glu Tyr Asp Val Leu Asp
            20

<210> SEQ ID NO 23
<211> LENGTH: 7
<212> TYPE: PRT
<213> ORGANISM: Hamster sp.
<220> FEATURE:
<221> NAME/KEY: MOD_RES
```

-continued

```
<222> LOCATION: (2)
<223> OTHER INFORMATION: PHOSPHORYLATION

<400> SEQUENCE: 23

Gln Tyr Glu Glu Ile Pro Ile
  1               5

<210> SEQ ID NO 24
<211> LENGTH: 10
<212> TYPE: PRT
<213> ORGANISM: Hamster sp.
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (5)
<223> OTHER INFORMATION: PHOSPHORYLATION
<220> FEATURE:
<221> NAME/KEY: MOD_RES
<222> LOCATION: (10)
<223> OTHER INFORMATION: AMIDATION

<400> SEQUENCE: 24

Lys Gly Gly Gln Tyr Glu Glu Ile Pro Ile
  1               5                   10

<210> SEQ ID NO 25
<211> LENGTH: 4
<212> TYPE: PRT
<213> ORGANISM: Homo sapiens

<400> SEQUENCE: 25

Tyr Glu Glu Ile
```